US006342385B1

(12) United States Patent
Qi et al.

(10) Patent No.: US 6,342,385 B1
(45) Date of Patent: Jan. 29, 2002

(54) MUTACIN I BIOSYNTHESIS GENES AND PROTEINS

(75) Inventors: Fengxia Qi, Birmingham; Page W. Caufield, Mountain Brook; Ping Chen, Homewood, all of AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/627,376

(22) Filed: Jul. 28, 2000

(51) Int. Cl.$^7$ .......................... C12N 1/20; C12N 15/00; C12N 5/00; C07H 21/04

(52) U.S. Cl. .............................. 435/252.3; 435/320.1; 435/325; 536/23.7

(58) Field of Search ........................... 435/252.3, 320.1, 435/325; 536/23.7

(56) References Cited

U.S. PATENT DOCUMENTS

| | | |
|---|---|---|
| 4,554,101 A | 11/1985 | Hopp et al. |
| 4,603,102 A | 7/1986 | Himmelmann et al. |
| 4,740,593 A | 4/1988 | Gonzalez et al. |
| 4,980,163 A | 12/1990 | Blackburn et al. |
| 5,043,176 A | 8/1991 | Bycroft et al. |
| 5,135,910 A | 8/1992 | Blackburn et al. |
| 5,932,469 A | 8/1999 | Hillman |

FOREIGN PATENT DOCUMENTS

| | | |
|---|---|---|
| GB | WO92/18143 | 10/1992 |
| WO | WO93/19087 | 9/1993 |

OTHER PUBLICATIONS

Augustin et al. (1992), "Genetic analysis of epidermin biosynthetic genes and epidermin–negative mutants of *Staphylococcus epidermidis*", Eur. J. Biochem., 204:1149–1154.

Bedwell et al. (1989), "Sequence and Structural Requirements of a Mitochondrial Protein Import Signal Defined by Saturation Cassette Mutagenesis", Mol.Cell. Biol., 9:1014–1025.

Buchman et al. (1988), "Structure, Expression, and Evolution of a Gene Encoding the Precursor of Nisin, a Small Protein Antibiotic*", J. Biol. Chem., 263:16260–16266.

Burdett (1990), "Nucleotide sequence of the tet(M) gene of Tn916", Nucl. Acid Res., 18:6137.

Caufield et al. (1990) "Evidence that Mutacin II production is not mediated by a 5.6–kb plasmid in *Streptococcus mutans*", Plasmid, 24:110–118.

Caufield et al. (1990) "Use of transposon Tn916 to inactivate and isolate a muticin–associated gene from *Streptococcus mutans*", Infection and Immunity, 58(12):4126–4135.

Caufield et al. (1985) "Distinct bacteriocin groups correlate with different groups of *Streptococcus mutans* plasmids" Infection and Immunity, 48(1):51–56.

Chikindas, M.L. et al. (1995) "Mutacin II, a bactericidal lantibiotic from *Streptococcus mutans*", Antimicrobial Agents and Chemotherapy, 39(12):2656–2660.

Chou and Fasman (1974a),"Prediction of Protein Conformation", Biochemistry, 13(2):222–245.

Chou and Fasman (1974b),"Conformational Parameters for Amino Acids in Helical, B–Sheet, and Random Coil Regions Calculated from Proteins", Biochemistry, 13(2):211–222.

Chou and Fasman (1978a),"Prediction of the Secondary Structure of Proteins from Their Amino Acid Sequence", Adv. Enzymol. Relat. Areas Mol. Biol., 47:45–148.

Chou and Fasman (1978b),"Empirical Predictions of Protein Conformation", Ann. Rev. Biochem., 47:251–276.

Chung and Hansen (1992),"Determination of the Sequence of spaE and Identification of a Promoter in the Subtilin (spa) Operon in *Bacillus subtilis*", J. Bacteriol., 174:6699–6702.

Dodd et al. (1990), "Analysis of the genetic determinant for production of the peptide antibiotic nisin", J. Gen. Microbiol., 136:555–566.

Gawron–Burke and Clewell (1984), "Regeneration of Insertionally Inactivated Streptococcal DNA Fragments after Excision of Transposon Tn916 in *Escherichia coli*: Strategy for Targeting and Cloning of Genes from Gram–Positive Bacteria", J. Bacteriol., 159:214–221.

Gross and Kiltz (1973), "The Number and Nature of α,β–UnsaturatedAmino Acids in Subtilin", Biochem. Biophys. Res. Commun., 50:559–565.

Hillman, J.D. et al. (1998), "Genetic and Biochemical Analysis of Mutacin 1140, a Lantibiotic from *Streptococcus mutans*", Infection and Immunity, 66(6):2743–2749.

Horinouchi and Weisblum (1982), "Nucleotide Sequence and Functional Map of pC194, a Plasmid that Specifies Inducible Chloramphenicol Resistance", J. Bacteriol., 150:815–825.

Horn et al. (1991), "Nisin biosynthesis genes are encoded by a novel conjugative transposon", Mol. Gen. Genet., 228:129–135.

Jakes et al. (1988), "A Hybrid Toxin from Bacteriophage f1 Attachment Protein and Colicin E3 has Altered Cell Receptor Specificity", J. Bacteriol., 170(9):4231–4238.

Kaletta and Entian (1989), "Nisin, a peptide antibiotic: cloning and sequencing of the nisA gene and posttranslational processing of its peptide product", Journal of Bacteriology, 171(3):1597–1601.

Kyte and Doolittle (1982), "A Simple Method for Dispalying the Hydropathic Character of a Protein", J. Mol. Biol., 157(1):105–132.

(List continued on next page.)

*Primary Examiner*—Mark Navarro
*Assistant Examiner*—Vanessa L. Ford
(74) *Attorney, Agent, or Firm*—Gifford, Krass, Groh, Sprinkle, Anderson & Citkowski, P.C.

(57) ABSTRACT

According to the present invention, an isolated and purified DNA sequence which encodes a lantibiotic, mutacin I, is disclosed. The nucleic acid sequence is set forth in SEQ ID No: 1 and the amino acid sequence is set forth in SEQ ID No: 2.

4 Claims, 7 Drawing Sheets

OTHER PUBLICATIONS

LeBlanc et al. (1988), "Nucleotide Sequence Analysis of Tetracycline Resistance Gene tetO from *Streptococcus mutans* DL5", J. Bacteriol., 170(8):3618–3626.

Liu and Hansen (1992), "Enhancement of the chemical and antimicrobial properties of subtilin by site–directed mutagenesis", J. Biol. Chemistry, 267(35):25078–25085.

Liu and Hansen (1991), "Conversion of *Bacillus subtilis* 168 to a Subtilin Producer by Competence Transformation", J. Bacteriol., 173(22):7387–7390.

Loyola–Rodriguez et al. (1992), "Purification and properties of extracellular mutacin, a bacteriocin from *Streptococcus sobrinus*", J. Gen. Microbiology, 138:269–274.

Macrina et al. (1977), "Survey of the Extrachromosomal Gene Pool of *Streptococcus mutans*", Infect. Immun., 17(1):215–226.

Miller et al. (1991), "Quantition of Type I, II, and V Collagens in Human Tissue Samples by High–Performance Liquid Chromatography of Selected Cyanogen Bromide Peptides", Anal. Biochem., 196:54–60.

Miller et al. (1990), "Amino Acid Analysis of Collagen Hydrolysates by Reverse–Phase High–Perfomance Liquid Chromatography of 9–Fluorenylmethyl Chloroformate Derivates", Anal Biochem., 190:92–97.

Nakano and Kuramitsu (1992), "Mechanism of *Streptococcus mutans* Glucosyltransferases: Hybrid–Enzyme Analysis", J. Bacteriol., 174(17):5639–5646.

Novak et al., (1996) "Detection of Modified Amino Acids in Lantibiotic Peptide Mutacin II by Chemical Derivatization and Electrospray Ionization—Mass Spectroscopic Analysis", Analytic Biochemistry, 236:358–360.

Novak et al. (1994), "Isolation and biochemical characterization of a novel lantibiotic mutacin from *Streptococcus mutans*", J. Bacteriol., 176(14):4316–4320.

Novak et al. (1994), "Genetic and biochemical characterization of a novel lantibiotic from *Streptococcus mutans*", 7th International Congress of Bacteriology and Applied Microbiology Division, Jul. 3–8, 1994.

Novak et al. (1993), "Biochemical Analysis of a Group II mutacin from *Streptococcus mutans*", 93rd General Meeting, Atlanta, Georgia, May 1993.

Novak et al. (1994), "Characterization of a novel lantibiotic from *Streptococcus mutans*", IVth International ASM Conference on Streptococcal Genetics, Sante Fe, New Mexico, May 15–18, 1994.

Ochman et al. (1993), "Use of Polymerase Chain Reaction to Amplify Segments Outside Boundaries of Known Sequences", Method. Enzymol., 218:309–321.

Parrot et al. (1990), "Preliminary characterization of four bacteriocins from *Streptococcus mutans*", Can . J. Microbiol., 36:123–130.

Schnell et al. (1992), "Analysis of genes involved in the biosynthesis of lantibiotic epidermin", Eur. J. Biochem., 204:57–68.

Sevag et al. (1938) "The isolation of the components of Streptococcal nucleoproteins in serologically active form", J. Biol. Chem., 124:425–436.

Tagg et al. (1976), "Bacteriocins of Gram–Positive Bacteria", Bacteriol. Rev., 40(3):722–756.

Tagg et al. (1990), "A longitudinal with study of Lancefield group A streptococcus acquisitions by a group of young Dunedin schoolchildren", N.Z. Med. J., 103:429–31.

Trieu–Cuot et al. (1990), "Nucleotide sequence of the erythromycin resistance gene of the conjugative transposon Tn1545", Nuc. Acid Res., 18(12):3660.

Tudor et al. (1990), "Size of the *Streptococcus mutans* GS–5 Chromosome as Determined by Pulsed–Field Gel Electrophoresis", Infect. Immun., 58(3):838–840.

Van Der Meer et al. (1993), "Characterization of the *Lactococcus lactis* Nisin A Operon Genes nisP, Encoding a Subtilisin–Like Serine Protease Involved in Precursor Processing, and nisR, Encoding a Regulatory Protein Involved in Nisin Biosynthesis", J. Bacteriol., 175(9):2578–2588.

Woodruff et al. (1998), "Sequence Analysis of mutA and mutM genes involved in the biosynthesis of the lantibiotic mutacin II in *Streptococcus mutans*", Gene 206:37–43.

Van Der Rijn and Kesler (1980), "Growth Characteristics of Group A Streptococci in a New Chemically Defined Medium", Infect. Immunol., 27(2):444–448.

FIG - 1A
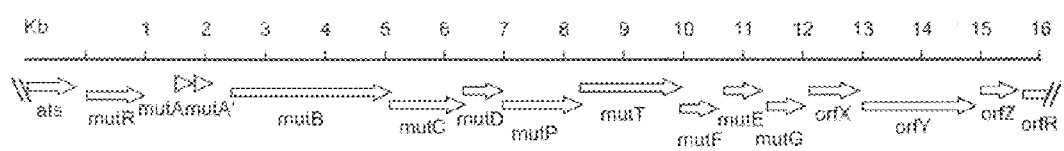
FIG - 1B
```
                  Leader Peptide                                    Mature Peptide
MutA:  1   MSNTQLLEVLGTETFDLFAFDTTDTTIVASNDDPDT--RFSSLSLCSLGCTGVKNPSFNSYCC  65
           M NTQLLEVLGT TFDLF F  TDT ++  D P T  +  S S+C    T V    SFNSYCC
MutA': 1   MLNTQLLEVLGTKTFDLFEFNITDTIVLQVSDSPGTHSKVGSFSICPPRKTSV---SFNSYCC  64
```
FIG - 1C

```
                            SEQUENCE LISTING

<160> NUMBER OF SEQ ID NOS: 17

<210> SEQ ID NO 1
<211> LENGTH: 168
<212> TYPE: DNA
<213> ORGANISM: Streptococcus mutans

<400> SEQUENCE: 1
atgtcaaaca cacaattatt agaagtcctt ggtactgaaa cttttgatgt tcaagaagat      60
ccaacagata ctactattgt ggcaagcaac gacgatccag atactcgttt ctcaagtttg     120
agtttaacag gggtgaaaaa tcctagtttc aatagttact gttgctaa                 168

<210> SEQ ID NO 2
<211> LENGTH: 24
<212> TYPE: PRT
<213> ORGANISM: Streptococcus mutans

<400> SEQUENCE: 2

Phe Ser Ser Leu Ser Leu Cys Ser Leu Gly Cys Thr Gly Val Lys Asn
1               5                   10                  15

Pro Ser Phe Asn Ser Tyr Cys Cys
            20

<210> SEQ ID NO 3
<211> LENGTH: 15567
<212> TYPE: DNA
<213> ORGANISM: Streptococcus mutans

<400> SEQUENCE: 3
aaatttgttt tttatactaa aagcgggaat gattcaaaac taaaaaagat aaacgaagaa      60
ttgaaaaagt gatataatag cacagaagag ggcctttata atgaaaggag actattttga    120
aagtaaatca atcaatggaa ttaggtgaac tttatcgaga attaagaatt gctagaggtt    180
tgaagataaa agatatagct tgtaaaaatc tgtccaagtc acaactctct agatttgaaa    240
```

-continued

```
atggacaaac catgttggca gctgataaat tgctattagc tatttcggga attcatatga    300
gttttcgga atttggatat gctttgagcc attatgagga gagtgatttt ttcaaaaggg    360
gtaataagtt atcagaatta tatgtccaga aagatatcaa aggattaaaa aagttattag    420
aatttaatga caatcatgag gtatttgatg tctacaatcg tttaaataaa ttggttattc    480
aagttactat tcatttgcta gatactgatt acataatatc agatgatgat aagaattttt    540
taacaactta tctatataat attgaagagt ggactgagta tgaactttat atctttggaa    600
atactatgtc tatattgtca tctgatgatt aattttttt gggaaaagct tttgtagaac    660
gtgataagtt gtatatatct cttcctagtc ataagaaaaa tgcagagtta acttttttaa    720
atttaatctt aattttgctt gaaagaaaaa aattatatca agcaatctat tttgtagaga    780
atttagagaa attattaaat taccaagata tgtttgcaat aacattttta aaattttaa    840
aaaaaattat tacttacttt catgataagt cagtagatat gtctgaatta gaacattata    900
ttaatatagt tgaagaaata aatcctacga ttgcttcaat tcttaaatct aatttgaatc    960
agctttatc aagttttagc cattaaagcc atcttgataa attttatatc tttcatattc    1020
attaaatgtg gagataatga aaaagcaacg gttatgctat cgctgctttt tttgtgatta    1080
gaagctatgt tatcatggag ttatagtaat gaaacatagt gacagttcat catttcttat    1140
tataaaagtg gtaataagag aagtggtaaa caaagagtta gtaaaataat acgtttaacc    1200
ataatatttc ctcctttaat ttattataag attcaaaaag gtaatattcc tatatttgca    1260
aatatgggat aaaataattt taaaaaagca gatttgcaat tttaaaaaaa atagaggcta    1320
atggtggtat tatattattg taaatatatg tttactcagt aatagtgatt tactattaca    1380
acagattttg ttgttatctt agatatttct gctagcatta gttatctgta gatgtactac    1440
ttaataagta tataattata attatataat aactattatc agattaccgt taaaagtttt    1500
ctgatatgct tctactgaac aatttacgtt cagttacaca catgaaaaag gaggatatta    1560
tgtcaaacac acaattatta gaagtccttg gtactgaaac ttttgatgtt caagaagatc    1620
tctttgcttt tgatacaaca gatactacta ttgtggcaag caacgacgat ccagatactc    1680
gtttctcaag tttgagttta tgttcattag gatgtacagg ggtgaaaaat cctagtttca    1740
atagttactg ttgctaagtt gtacaaaaga tttagattgt gtcgcatgtc agcggcacaa    1800
tcttttgata ttagagatat taaatatgtt aaacacacaa ttattagaag tccttggtac    1860
taaaactttt gatgttcaag aagatttatt tgagtttaat ataacagata ctattgtact    1920
gcaggttagt gatagtccag gtactcatag taaagtgggt agtttcagta tctgtcctcc    1980
tcgaaagacc tccgtcagtt tcaatagtta ctgttgttaa ctataaatta tacttaaatt    2040
gataggaaac ttggtcatga cattatcata tgttgatatt ggaagagaat caaatttata    2100
aagcaattaa atctaaatt tgatgaatat ttagatgaat tattactagg ttgacagtca    2160
tgttaggaga agagatgaac gattttcaat ttcaagatta ttttatgtac agaaaaccat    2220
taggcaactt ttctaatttt cttagtataa ctgatatgat ggatcctatt gaattattac    2280
ataatgatcc gatatttgct gaaggggtat atttggcttc cccatctctt agatcatcta    2340
taaataaatt agagaatcag attgcaagta ctaaggaaaa aaagaatgca aaagagacta    2400
tttttcaata ctatgcccgt tataacacga gatcaactcc gtttggcttg ttttcgtcca    2460
tcggaatagg tggttttcg aaccacccta ggaaagagaa atcttgttat gaaaaatctg    2520
ttaatgttga tcttttttgg gcttataaag tagcagataa actagaaagt atgcctgaaa    2580
ttttaaatac tttaaaagta gttgctaata atgctttgca aaagtcaaat gattttggc    2640
```

-continued

```
ttttagatac acgaagtcat tttggactta tgaattcacg ttcagatatt cgtgaggaca      2700
ttacagttaa gtctaatcag cttatagatt atgttattaa ttgcacagaa gaaccaatta      2760
gctatcaaac attaattgat gatattgccg agaaattctc tcaatctagt gatgatgtaa      2820
aagaatattt gcaaacatta attaaagagg agttttttaat aactgaattg aaatttagtt     2880
tgattgatga taatcctttg gattggttta ttaatatttt agaaagagat caaaataact      2940
cagaattact tgaaaagttg actgaaataa aggcaatgat tcaagattat actgaccgta     3000
acataggtga aggtaacaat tcgatttttag ctctagaaaa taagatgagc caaatagtaa    3060
aagccaacgc atacctgcga gttgatcttt atgatcatgc agagctgaag ttagcgcaac     3120
ataccaagag ttctcttcag aatattttga agtactaag ttcttttttcg tcagctgtta    3180 atagtcaaaa agaaattaaa aattatcatg agaaatttat tgccaggtat ggatacgagc     3240
agttagtacc tcttcaatta cttttgaatt ctactagtgg acttggtttt ccaaaagggt     3300
atagtcaaac agaagtttct aaacaaaata atgaagatag taaaaatcaa aaaataatag     3360
aatttttaca gagaaaattt gaaaaagctt taagagatgg taaagaaatt attttgagtg     3420
atgatgattt aaaagattta aattttgaca cggaacagca aatatcagga gaattatatt     3480
gtttctacaa ttttaaaagt aaaaagctag aggttagtag tttaggtgtc tcacagatgc     3540
ttggaaatac ttttggacgt ttccattcta aattgccgaa tacgatagtc acaaaaaatg     3600
taaataagac gaaagaaatt tttactgagg cttatccaaa tactattatt actcaattaa     3660
atgaagtgcc atattttggg agaggtggca atattatgat tagtaatagc cttaaaagtc     3720
accagttgga attgaggaac tatactacta aaaaagagat gagtatcaat gatatttatg    3780
tacgtgcaac cagtgaggag ttatatttt attctaagaa atatgagaaa agagttattt      3840
ttgtgatgaa taatatgttt aattatataa atggttctaa actcttacgt tttttactag     3900
aagtttcaaa ttctgatttt caaaatatta ccccgattac gcttggtagt ctggattctt     3960
ataatcatgt gcccgctatc atttataaag atattattat taaaccggaa acatggaaca    4020
ttagaaaatc tgaagctaag actttagatt ctctcaaaaa ttggctaact aataataatg    4080
ttccgccttt tgtacggatg aaatatactg atcaaattat ttatttagat ttgagtcgga    4140
ctattgattt aactatgcta tttcagagta tcaaaaaaca tagcttcata caattattag    4200
atgttcattc agtatgtaca aacgatacgg agattttaga attagttgtt ccttttacaa    4260
gaagtgatgt taacgctcac cagatttatc attatgctca gaatatttat actttggagg    4320
attcaggtag taaagaaaaa tattttttacg ctaaaattta tgtgaataaa caacgacaga    4380
cctctttcct acaaaaagag tatcctttat tattaaaata tttgaaactc ccagaaaact    4440
tacaatggtt ctatattaga tataaagatg atggaaaaga cagcatacgt ctcagaatca    4500
gatatgtaga agataaacaa ttagttcaac tttattcacg ctttatagag tgggcaacaa    4560
aagcacggaa aaatatccaa atttcaggtt atgaaattag tgaatatatc cctgaatcag    4620
caagatatgg agggaaaaaa tattcttcaa ttattcattc ttttttctat tatgatagta    4680
ttttggattt gcttttacag aagaaagcag aacaaactat tgaagtaaga acatctctca    4740
gtattattcg tatgttttta atgatgaaat taagcttaca agaccagcag aaactcataa    4800
agaatttatt tgatggaaaa cataaactta aatatgaaaa agaatatcat aattcaataa    4860
gtttattact tgcaatttta tgtacaaaaa atcagacaga tgaagctgat attttctgtg    4920
taatgaatat gaaaaaaatc actgaaaaaa ttagctcagt tcttaaacaa aaggacttaa    4980
```

-continued

```
caacagattg gcagagaatt ctaggaagtt taattcatat gcgatgtaat cgagtatatg   5040
gaattaacag tgagttagaa agaaaaacaa tgtttattgt tgacaaagtt attaattcaa   5100
aaagatatac ggtatgtttt ttggaggtgg gtaatgagac aaagtaaacg tgtcgaaaaa   5160
attaaagata ttctaactga gcaaacttat ttattcgatt atcaagaaat attaaaaaaa   5220
gtcagtcaag caaaacaaac agattttggg aatttacttt ccttatcttc gggaataact   5280
tctttattaa tattttatca agagtatgag aatttagaag gagtaaactt aaagcagcaa   5340
aagcagtcat taattgggct tataagtcat tatattaatc aaatagcaga gaatcctct    5400 ttatttgatg gtttagctgg ggtaggtttt gctattaatt atatctctaa taacggtaaa   5460
tattatcaaa aacttcttga acagattgac aacagactcc gtcagaatat tgaacggaac   5520
cttgtcaact ataagaatga ggaatatgca aatcctatga attatgatgt agtttctgga   5580
aatgctggag tagctcgcta cttgatggaa agagaatcct ctgaagattg gcgaatagtt   5640
gaaatgattt tagaaacatt ttataaagct ttagagcaag gctggcgagt acagtcaaaa   5700
tatcaatttc tagagtctga aaagcagtat tatctagaag gaaatataaa tttcgggttg   5760
gctcatggaa tattaggacc tgcgacaatt atggctcttt atcaacgaag agaaccacaa   5820
aatacaagaa atgctgagaa gcttcaagaa acttatcgac taataaaaag atacgcccag   5880
gtaagagatg aagggttacg atggccaata cgatatgatt tgtttcgtaa agagggttct   5940
tttatattac gaaatggttg gtgttatggc gagaatggca tttataatac acttttcctt   6000
atgggaaaag tactctcaaa tcaggagatt tgtgaaactg ctcagaaagt tataccatcc   6060
atcataaaag atgattatga gaaaatggaa agtccaacat tttgtcacgg gtttgctgga   6120
aaagcaaatt tctttcttct gcaatatcaa agaactaaag aatcaatatt tttagttaaa   6180
gcagaagaag aaattgataa aatattaatt gtgtacaatt ctgaaaatat gtttggattt   6240
aaagatatag aagataatat tgataatact ggagagagat taacttattg ggataatttt   6300
ggtcttctta gtggaactgt tggtgttcta ttagttttga tggaatattg taatattgta   6360
aatgccggaa aaattgcaga gtggaataaa attttctttt tgacttaatt aactgaacgg   6420
agaaataatt atggaagaac aaaatataga gaaaaaaatt ctcttgtgcc taacaggttc   6480
tggagcattg ttagggatag ctgaatatat tacgttttgg actgtgcgct ttaagcatgt   6540
tcgagttatt gtctctgata atgctgcgaa gatgcttcct gttgctgcta ttacacaatt   6600
gtgtgagaaa gtgtatactg atgaagtttc ctttacagat aagcaaaaga atcacatagc   6660
tttaactcgc tgggcagaca taacagttgt cttacctgct acagcaaata taattggaaa   6720
agttgctaat ggtattgcag ataacttat gacaacaact cttctttctt ctagcaagcc   6780
agttttaatt tatccttgca tgaataatat tatgtgggaa aatccagtag ttcaaaaaaa   6840
tgttgaagtt ttatctggaa cccaatataa ggtaattgtt ggacaagaat cagaatcttt   6900
tgaattagcc agtggaaaga tgaaaagaa tattgcaatt ccaagtttgg atgaattgca   6960
acgagttgtt ttagaaaatt tacaagaaga gaggtaagag tatgaagaag aaaggattac   7020
tagtaataat ctttctaact ttcttttttct tttatcctaa agctaaagct gctgaatata   7080
caattatatc aaataatagt gaacaaactg ttaatgactt gaataattta ggagttacag   7140
tcaatagcca tattgcggaa attggatata ttgaagctca aggagatgtt aacattgatc   7200
agattaaaaa gctgtcaaat attcaaagta tccagaatat ggctgataca tcacagaata   7260
tcacgactag agttccttca acatatatta accagacaat acaattgcct cagcttttt    7320 cttatcagtg ggatatgcaa aaaattacta ataatggtgt ttcatattca ttaaataaag   7380
```

-continued

```
aaaatcgaaa aaatgtaaca gttgctttag ttgattctgg gattgatgta gaccataatg    7440
cttttacagg aatgattgat agtcgttcaa aaaattttgt gcctgctgga ggatatgata    7500
atagtgaaag cagtgaaact ggaaatatta atgatattga tgataaaaaa ggccatggaa    7560
cagcagttgc tgggcaaatt gctgcaaatg gtcaaatctt tggtgtgtcc ccaggaacga    7620
accttcttat ctatagagtt tttggaaaat caaaatcaaa ggagtgctgg attttaaaag    7680
caattattga tgcaacaaat aacggtgcta atgttattaa tctaagtttg gggcaatata    7740
ttaagattcc taatggtgat atttgggagt ctgccgaagc attaggatat aagtttgcca    7800
ttgattatgc cacaagacat aatgtcattg ttgtagcagc cacaggtaat gatggattaa    7860
gtgatgacaa cggagaggtt aaaacttatt ataatagtca gcattcagga caagatatgt    7920
ctcaaaatga cacggttgaa gattatcctt ctgttttacc taatgctatt gcagttggct    7980
cttctgataa taataatcaa agatcatctt ttagtaatta ctataatcaa tatcaggaca    8040
attttatttt ggctcctggt ggtggaacaa ctttactaga ccaatatggt caagaagagt    8100
ggtataatca gaaactttt atgaaagaac aagtcttatc aacaagtaat aatggaaatt    8160
atgattatgc agatggtact tctatttcaa caggaaaagt ttctggagag cttgcagaaa    8220
ttattagtaa ctaccatctt caaggagatt cttcaaaagc tagaagtatt ctactaaatc    8280
aagttaatta tactagtgat ggttataaag aaataagcac ttacaaagct tgcgaggtt    8340
actaaatgaa gtggttagaa gttttgcaaa ttagtaaaaa agaaaaaatt ctttatctta    8400
ttggttgtat attttcaatt atgacaggct taattactct acgaatcacc tacttactta    8460
agaatttagt tgacagcaaa tcgtctttta ataatttgtt cttgtttctt gttttgggat    8520
tagttctttt tatcatagat gctggttcac agtatctaat ttcattgatt ggtaatcaag    8580
tagtgtttaa cagtcgaaat aatatttgga aaaaaatttc tgattggaca gatagtaaag    8640
atgattcttc tgaaatggca ggccaccta ttaatgatag tgaactgata gaaaattta    8700
taatttctac tattcctcaa tcaataaatt cagttattgt tggatcagga tccttagtta    8760
tgctatttgt tattaatagt aaaatgtctt tagaagttat agggatttgc ttgctttat    8820
tgttcattat gcaacccttt tctagaatat aagcaaaat aagtaaaaga atccaggaag    8880
acaaagctga acttattaat attgcctcac agttgagagg acaagtcaaa acaataaaaa    8940
gctataatgc tcaagattat gccttttcaaa aatttgatga gcaaaatcgc caattatttc    9000
aagatatctt aaatagaata aaaattttta gcatttactc tccttttta aatatcttaa    9060
ttcttttat gattataatt gttgtttggc taggaaatac agaagtacgt tcaggaaatc    9120
tcactgtagg ttcagcaact atttttgttg tttatatgac acaattaatt aatccaatta    9180
tgcaattatc acaattagtt gctcatatgg ggatgcttaa tggcggcgtg aacgtctttt    9240
tggagtataa tcaagctatt ccagaaaaaa atggaatcaa gaaaattgat gaaataatta    9300
atatcgcgtt tgataatgtt tcatttgctt atgataacca agaaaatatt attgaaaatg    9360
tgaatttaac ttttcaaaaa ggtacttata tttccattgt tggtgaaagt ggagttggga    9420
aatcaacctt acttgatctt ttagaacata attatgtacc atcaaaagga cgaatcttaa    9480
taaacggaat agacttagaa gaattgaata ttaagacttt gcgaaataag ataagctatg    9540
tatctcaaga accaacaatt ctttctggga caattcgtga actattagac tttaatcagc    9600
aacagcatac agaaactagt ctttggaatg ttcttgatac tgtagaatta tcagaactta    9660
ttagaaattt acccgcgaaa ttgattcta aggttgatga atatggtggt aacctctctg    9720
```

-continued

| | |
|---|---|
| gaggtcagat gcaacggatc tcacttgcaa gaggattact gaaagcagga gatgttttat | 9780 |
| tattagatga atcttttgcc aatattgatg aagagacttg tcttaaaata aaattaaaaa | 9840 |
| ttgctgctta tgctgaatca cacaagcaaa ttgttattga agttattcat aatctaaata | 9900 |
| gaataactcc cagtagtatc gtttaccgat tggctgataa aaaactagaa attttgagga | 9960 |
| gcggatttta atagaaaagt cgaagaaatc tgagtaaaag atcagtttct ggtcgaaaat | 10020 |
| taaatattgt gatatataaa taagcttaaa atcaatattc ctaataattt gattttaagc | 10080 |
| tttttactat ttgatgagtt tttactcaag atcttttgat tttcctgata aagtccttaa | 10140 |
| atttgttttt tatactaaaa gcagaaaagg aggatatcat aatggattat atgctagaga | 10200 |
| cgaaaaattt aactaaacag tttggtaagc aaacagcggt taaccaattg aatttgaaag | 10260 |
| ttgaacgtca ttcaatttat ggtttgctgg ggcctaatgg ttccggcaaa tcaacaacac | 10320 |
| ttaaaatgat tactgaaatg ctaagaaaga catctggtca cattcttata gacggacacg | 10380 |
| attggagccg caaggattta gaaaatatcg gggctctgat tgaatcaccg ccgctttatg | 10440 |
| aaaacctgac tgcgcgtgaa aatttaaagg taagaacctt gatgctgggt ttacctgata | 10500 |
| gtcgcattga tgaggtttta aaaatagtgg atctaaccaa cacgggtaaa aaaagagcag | 10560 |
| ggcaattttc tatgggcatg aagcagcgtc tgggtattgc tatcgcactt ttgaactcac | 10620 |
| ctcaactttt gattctggat gaaccgacta atggacttga tcctattggt attcaggagt | 10680 |
| tgcgtaatct tattcgttcc ttccctacac aaggaattac agttattatt ccagtcata | 10740 |
| tcttatctga gattcagatg acagcggatc atattggtat cattgctaat ggcgtactgg | 10800 |
| gttatcagga tagaattcac caagatgaag acttggaaaa acttttttact gatgtggtta | 10860 |
| tgagataccg aggaggtgag tgatatgctg ggcatgtttc aggcagaaag gttaaaactg | 10920 |
| aagcgaagta tggcgaagaa gttactagtt tttgcccccca taatagctat tttatatggt | 10980 |
| tttatagcac ctgtggggta tttagtaaat aatgcttata attggtggta tgtcatgatt | 11040 |
| tttccagggc tgctaacctt atttgctgct ttaataaata cttacgaaga aaaaaagctg | 11100 |
| cattatcgag cagtgttttcc tttgcccatt tcttttaagaa aattttggtt tgaaaaaatt | 11160 |
| tttataactg tttattatct taattttagt aatggagtac tttggataat tacagtatta | 11220 |
| ctgaatactt ttatttacc aaattatgga aaagactata cttatactgt tggagaatta | 11280 |
| gcactagctt ctttggttat aatagttact acactttggc aaattccatt ttgtctgtgg | 11340 |
| ctgacaaaaa gaatcggttt taccataacg ttgataatta atttaatgag taatttcatt | 11400 |
| ttgggagttg tttttgcaac tacttcctgc tggtggcttt gtccatatag ttggggaata | 11460 |
| cgattaatgg tacccatttt aaaaatacta ccgagtggtc taaaggcagg tatagcagga | 11520 |
| gctccatcat tgccaacaag ttttttggagt atcgttatta gtttgtgttt agcggttatc | 11580 |
| ttatttgtta gtttgacagt tttgagtgca tcttggtttg aaaaacagga agtgaaatga | 11640 |
| tgattgattt attaaaagca gaaaatgtaa ataccgtca tactttttta ccatggttac | 11700 |
| acctgatttt acctgttact acagctattg ttgttattgt ttatgggcta atgacgccga | 11760 |
| ctcactcttg ggctgatatt actggtggtt acttagaact attgggtata agttttccaa | 11820 |
| ttgtcattgc tgttatttgt gggaaatcag ttggactaga agtagaggct ggtcaatttc | 11880 |
| aagttatgtt agcaattaag caaaggaact tgatattttg tatcaagtta ttgaatttgc | 11940 |
| tcattttaga actttttttca actctattag ctataggaat ttatggatta atttatcaat | 12000 |
| taagtaataa acatttgata ttttatggat atgctgtaat tttactaaca gcttcaatgc | 12060 |
| tcattctttta tctgattcac ttagttgtag tattttttgtt tggcaatagt gctaatattg | 12120 |

```
ggttggggat tgctgaatct ttactatctg ctttgctctt gacaggttta ggagatggta   12180
tctggcaatt tattccttgt gcttggggta ctcgcctaat gggtacctta ataaatctgt   12240
ggtattactc tgggcacagc ttatttttta agcaacagct tttaatttgg ctggaagtcg   12300
cagttccact aactttaatg gctttaatcc ttagtataat ttggttcgac agatggcaag   12360
gacgtagcag tgatgaataa aggaaaaagg agaactttca acatgacct atattggtgt    12420 tagtcatctc aaaaaggtgt ataaaactca ggaaggcctc actaacgaag cgttaaaaga   12480
tattacgttc tcagttcaag aagggggaatt tattgctatt atgggtgaat ctggctcagg   12540
gaagtcaact ctccttaata tcctagcttg tatggattat ccaagtagtg gtcatatcat   12600
cttcaataac tatcaattag agaaagttaa agatgaagag gctgctgttt ttagaagtcg   12660
gcatattggt tttatttttc aaaattttcaa tcttttaaat atcttcaata ataaagacaa   12720
tctgttgata ccagttatta tttcgggaag taaggtgaat tcctatgaaa aacgattacg   12780
tgatttagct gctgttgttg gtatagaatc tttgctatct aaatatcctt atgaattatc   12840
tggaggtcaa caacaaaggt tagctattgc cagagcttta attatgaatc cagacttgat   12900
attggccgat gagccaacag gacaattgga ctctaagact tctcagcgaa tcttgaattt   12960
gttgtctaac atcaacgcta aacgaaagac aattctaatg gtgactcata gtcctaaagc   13020
tgctagttat gcaaaccgag ttctttttat caaggatggt gttattttca atcaacttgt   13080
tcgtgggtgt aaatccaggg aaggcttttt agatcaaatt attatggctc aggccagtct   13140
gtaggaggtt gtcctgatta tgttttacc caaaattcc tttcataatc ttattgtaaa    13200
taaatcatta accttacctt attttgctat tatgaccatt tttagtggtt ttaactatgt   13260
tttgattaat ttttaaccca accctagttt ttataacatt ccaacagcta ggatactgat   13320
tgatattctt attttggtt ttatcttaat ttcattactg atgttgcttt atggtcgcta   13380
tgccaatcgt tttataagtg atgagcgtaa tagtaatatg ggaattttc tcatgttggg    13440 aatggggaaa aagcaattat taaaaataat ctatttggaa aagttatatc ttttttacagg   13500 aacgtttttt ggaggtttaa tctttggttt cgtatacagt aagatatttt ttctttttat   13560
cagaaatcta attgttattg gagatgtcag agaacaatat agcttaacgg ctattagttg   13620
gctacttatt cttactttt ttatttattt tattatttat ctatcagagt accgattatt     13680
aaaacgtcaa agtatcacgg ttattttaa tagcaaagct aagcgtgata atcctagaaa    13740
aactagtgtt tttgttggac tttttggact ttttgccctg ttaatgggat atcattttgc    13800
tttaacaagt cccaatgtca caaccagttt cagccgtttc atttatgctg cctgcttagt   13860
tactctaggt attttttgca cgttttcgtc aggtgtgatt atgttactga ctgtcataaa   13920
gaagagaaga gctatctact ataatcaacg cgctttgtt gtgattgcta gtttatttca    13980
ccgtatccgc agtaatgctc tgtctttggc gactatctgt attttagca ccgctaccct    14040 agttagttta tctgtcttag ctagtctcta tcttgcaaag gacaatatgg ttcgtctttc   14100
aagtcctaga gatgttacgg tgctatctac aactgatatt gaaccgaatt taatggacat   14160
cgctacaaaa aatcatgtta ctctaactaa tcgccagaat ttaaaggttt ctcaatctgt   14220
ttatggtaat atcaaaggaa gtcatttgtc agttgatcct aatggcggta tggctaatga   14280
ttatcaaata acagttattt cattggattc ttttaatgct tctaataata cccattatcg   14340
tttaaaaaat catgaaattc tcacctatgt ttcaaatgga gcagctgctc cctctagcta   14400
tacaactaat ggtgttaaac taaccaatgt taaacaaatt aaaaggataa actttatttt   14460
```

-continued

```
ttctccgcta cgctctatgc agcctaattt ctttataatt actgacaatc gagaaataat    14520
tcagactatt ttgaaagagg agctaacatg gggaacgatg gcaggctacc atgttaaagg    14580
aaaaaaaatg aatcagaaag attttttatga tgagcttgag actactaatt tcaggcaatt    14640
tagtgctaat gtagtttcaa taagacaggt caaatcaatg tttaatgctt tatttggcgg    14700
tttactcttt gttggtatta tttttggaac tattttttgca attttgacag ctataactat    14760
ttattatcaa cagctttctg aaggaattcg agaccgagat gattataagg ccatgataaa    14820
attaggtatg acaaataaaa ctattcaaga cagtattaag gttcaaataa actttgtttt    14880
catcttgccc attgcttttg ccctattaaa tctcatcttt gcacttccta ttttatataa    14940
aataatgaca acttttggat ttaatgatgc aggactattc ctaagagctg ttggaacttg    15000
tctgattgtt tacctttttct tttattggtt tatttgtcat tgcacatcca aactatatta    15060
tcgtttaata tctaaaaaat agaggagttt atattatgcg tattgtaagt tcattggtat    15120 cgctttttatt gactatcttt tggattttg ctatagcttt tatcccaatt ggagaccaga    15180
atagttttaa taaccagaa atgtggttct tgttttttt cgctattatt atttatagta     15240
ttgttataat aagcgattat tatctaaaga gctttaatct tttgaaagtt tatcaaattt     15300
tagttttgtt tattagcata ctgtgtgctc tttgtggttt atcactaact gctttaggat    15360
tgaaagtatt cactttagct attggaattg ttagtcttgt taatacaatt atttatttct    15420
ttttcgctaa taaaaagat aatgttgaat aaaatatgtt atcctagtga aggaggtttc    15480
ctagaatgac ccgtattttg gtaattgatg atgatgcaga tattttggct ctgataaaaa    15540
ataccttgca actgcaaaac tatctgg                                       15567
```

<210> SEQ ID NO 4
<211> LENGTH: 289
<212> TYPE: PRT
<213> ORGANISM: Streptococcus mutans

<400> SEQUENCE: 4

```
Leu Lys Val Asn Gln Ser Met Glu Leu Gly Glu Leu Tyr Arg Glu Leu
 1               5                  10                  15

Arg Ile Ala Arg Gly Leu Lys Ile Lys Asp Ile Ala Cys Lys Asn Leu
            20                  25                  30

Ser Lys Ser Gln Leu Ser Arg Phe Glu Asn Gly Gln Thr Met Leu Ala
        35                  40                  45

Ala Asp Lys Leu Leu Leu Ala Ile Ser Gly Ile His Met Ser Phe Ser
    50                  55                  60

Glu Phe Gly Tyr Ala Leu Ser His Tyr Glu Glu Ser Asp Phe Phe Lys
65                  70                  75                  80

Arg Gly Asn Lys Leu Ser Glu Leu Tyr Val Gln Lys Asp Ile Lys Gly
                85                  90                  95

Leu Lys Lys Leu Leu Glu Phe Asn Asp Asn His Glu Val Phe Asp Val
            100                 105                 110

Tyr Asn Arg Leu Asn Lys Leu Val Ile Gln Val Thr Ile His Leu Leu
        115                 120                 125

Asp Thr Asp Tyr Ile Ile Ser Asp Asp Lys Asn Phe Leu Thr Thr
    130                 135                 140

Tyr Leu Tyr Asn Ile Glu Glu Trp Thr Glu Tyr Glu Leu Tyr Ile Phe
145                 150                 155                 160

Gly Asn Thr Met Ser Ile Leu Ser Ser Asp Asp Leu Ile Phe Leu Gly
                165                 170                 175
```

```
Lys Ala Phe Val Glu Arg Asp Lys Leu Tyr Ile Ser Leu Pro Ser His
                180                 185                 190

Lys Lys Asn Ala Glu Leu Thr Phe Leu Asn Leu Ile Leu Ile Leu Leu
            195                 200                 205

Glu Arg Lys Lys Leu Tyr Gln Ala Ile Tyr Phe Val Glu Asn Leu Glu
        210                 215                 220

Lys Leu Leu Asn Tyr Gln Asp Met Phe Ala Ile Thr Phe Leu Lys Phe
225                 230                 235                 240

Leu Lys Lys Ile Ile Thr Tyr Phe His Asp Lys Ser Val Asp Met Ser
                245                 250                 255

Glu Leu Glu His Tyr Ile Asn Ile Val Glu Glu Ile Asn Pro Thr Ile
            260                 265                 270

Ala Ser Ile Leu Lys Ser Asn Leu Asn Gln Leu Leu Ser Ser Phe Ser
        275                 280                 285

His

<210> SEQ ID NO 5
<211> LENGTH: 65
<212> TYPE: PRT
<213> ORGANISM: Streptococcus mutans

<400> SEQUENCE: 5

Met Ser Asn Thr Gln Leu Leu Glu Val Leu Gly Thr Glu Thr Phe Asp
1               5                   10                  15

Val Gln Glu Asp Leu Phe Ala Phe Asp Thr Thr Asp Thr Thr Ile Val
            20                  25                  30

Ala Ser Asn Asp Asp Pro Asp Thr Arg Phe Ser Ser Leu Ser Leu Cys
        35                  40                  45

Ser Leu Gly Cys Thr Gly Val Lys Asn Pro Ser Phe Asn Ser Tyr Cys
    50                  55                  60

Cys
65

<210> SEQ ID NO 6
<211> LENGTH: 64
<212> TYPE: PRT
<213> ORGANISM: Streptococcus mutans

<400> SEQUENCE: 6

Met Leu Asn Thr Gln Leu Leu Glu Val Leu Gly Thr Lys Thr Phe Asp
1               5                   10                  15

Val Gln Glu Asp Leu Phe Glu Phe Asn Ile Thr Asp Thr Ile Val Leu
            20                  25                  30

Gln Val Ser Asp Ser Pro Gly Thr His Ser Lys Val Gly Ser Phe Ser
        35                  40                  45

Ile Cys Pro Pro Arg Lys Thr Ser Val Ser Phe Asn Ser Tyr Cys Cys
    50                  55                  60

<210> SEQ ID NO 7
<211> LENGTH: 990
<212> TYPE: PRT
<213> ORGANISM: Streptococcus mutans

<400> SEQUENCE: 7

Met Asn Asp Phe Gln Phe Gln Asp Tyr Phe Met Tyr Arg Lys Pro Leu
1               5                   10                  15

Gly Asn Phe Ser Asn Phe Leu Ser Ile Thr Asp Met Met Asp Pro Ile
            20                  25                  30
```

```
Glu Leu Leu His Asn Asp Pro Ile Phe Ala Gly Val Tyr Leu Ala
         35                  40                  45
Ser Pro Ser Leu Arg Ser Ser Ile Asn Lys Leu Glu Asn Gln Ile Ala
 50                      55                  60
Ser Thr Lys Glu Lys Lys Asn Ala Lys Glu Thr Ile Phe Gln Tyr Tyr
 65                  70                  75                  80
Ala Arg Tyr Asn Thr Arg Ser Thr Pro Phe Gly Leu Phe Ser Ser Ile
                 85                  90                  95
Gly Ile Gly Gly Phe Ser Asn His Pro Arg Lys Glu Lys Ser Cys Tyr
                100                 105                 110
Glu Lys Ser Val Asn Val Asp Leu Phe Trp Ala Tyr Lys Val Ala Asp
         115                 120                 125
Lys Leu Glu Ser Met Pro Glu Ile Leu Asn Thr Leu Lys Val Val Ala
         130                 135                 140
Asn Asn Ala Leu Gln Lys Ser Asn Asp Phe Trp Leu Leu Asp Thr Arg
145                 150                 155                 160
Ser His Phe Gly Leu Met Asn Ser Arg Ser Asp Ile Arg Glu Asp Ile
                165                 170                 175
Thr Val Lys Ser Asn Gln Leu Ile Asp Tyr Val Ile Asn Cys Thr Glu
         180                 185                 190
Glu Pro Ile Ser Tyr Gln Thr Leu Ile Asp Asp Ile Ala Glu Lys Phe
         195                 200                 205
Ser Gln Ser Ser Asp Asp Val Lys Glu Tyr Leu Gln Thr Leu Ile Lys
         210                 215                 220
Glu Glu Phe Leu Ile Thr Glu Leu Lys Phe Ser Leu Ile Asp Asp Asn
225                 230                 235                 240
Pro Leu Asp Trp Phe Ile Asn Ile Leu Glu Arg Asp Gln Asn Asn Ser
                245                 250                 255
Glu Leu Leu Glu Lys Leu Thr Glu Ile Lys Ala Met Ile Gln Asp Tyr
                260                 265                 270
Thr Asp Arg Asn Ile Gly Glu Gly Asn Asn Ser Ile Leu Ala Leu Glu
         275                 280                 285
Asn Lys Met Ser Gln Ile Val Lys Ala Asn Ala Tyr Leu Arg Val Asp
290                 295                 300
Leu Tyr Asp His Ala Glu Leu Lys Leu Ala Gln His Thr Lys Ser Ser
305                 310                 315                 320
Leu Gln Asn Ile Leu Lys Val Leu Ser Ser Phe Ser Ala Val Asn
                325                 330                 335
Ser Gln Lys Glu Ile Lys Asn Tyr His Glu Lys Phe Ile Ala Arg Tyr
         340                 345                 350
Gly Tyr Glu Gln Leu Val Pro Leu Gln Leu Leu Asn Ser Thr Ser
         355                 360                 365
Gly Leu Gly Phe Pro Lys Gly Tyr Ser Gln Thr Glu Val Ser Lys Gln
         370                 375                 380
Asn Asn Glu Asp Ser Lys Asn Gln Lys Ile Ile Glu Phe Leu Gln Arg
385                 390                 395                 400
Lys Phe Glu Lys Ala Leu Arg Asp Gly Lys Glu Ile Ile Leu Ser Asp
                405                 410                 415
Asp Asp Leu Lys Asp Leu Asn Phe Asp Thr Glu Gln Gln Ile Ser Gly
         420                 425                 430
Glu Leu Tyr Cys Phe Tyr Asn Pro Lys Ser Lys Lys Leu Glu Val Ser
         435                 440                 445
```

```
Ser Leu Gly Val Ser Gln Met Leu Gly Asn Thr Phe Gly Arg Phe His
    450                 455                 460

Ser Lys Leu Pro Asn Thr Ile Val Thr Lys Asn Val Asn Lys Thr Lys
465                 470                 475                 480

Glu Ile Phe Thr Glu Ala Tyr Pro Asn Thr Ile Ile Thr Gln Leu Asn
                    485                 490                 495

Glu Val Pro Tyr Phe Gly Arg Gly Gly Asn Ile Met Ile Ser Asn Ser
                500                 505                 510

Leu Lys Ser His Gln Leu Glu Leu Arg Asn Tyr Thr Thr Lys Lys Glu
            515                 520                 525

Met Ser Ile Asn Asp Ile Tyr Val Arg Ala Thr Ser Glu Glu Leu Tyr
    530                 535                 540

Phe Tyr Ser Lys Lys Tyr Glu Lys Arg Val Ile Phe Val Met Asn Asn
545                 550                 555                 560

Met Phe Asn Tyr Ile Asn Gly Ser Lys Leu Leu Arg Phe Leu Leu Glu
                565                 570                 575

Val Ser Asn Ser Asp Phe Gln Asn Ile Thr Pro Ile Thr Leu Gly Ser
                580                 585                 590

Leu Asp Ser Tyr Asn His Val Pro Ala Ile Ile Tyr Lys Asp Ile Ile
            595                 600                 605

Ile Lys Pro Glu Thr Trp Asn Ile Arg Lys Ser Glu Ala Lys Thr Leu
    610                 615                 620

Asp Ser Leu Lys Asn Trp Leu Thr Asn Asn Val Pro Pro Phe Val
625                 630                 635                 640

Arg Met Lys Tyr Thr Asp Gln Ile Ile Tyr Leu Asp Leu Ser Arg Thr
                645                 650                 655

Ile Asp Leu Thr Met Leu Phe Gln Ser Ile Lys Lys His Ser Phe Ile
                660                 665                 670

Gln Leu Leu Asp Val His Ser Val Cys Thr Asn Asp Thr Glu Ile Leu
            675                 680                 685

Glu Leu Val Val Pro Phe Thr Arg Ser Asp Val Asn Ala His Gln Ile
    690                 695                 700

Tyr His Tyr Ala Gln Asn Ile Tyr Thr Leu Glu Asp Ser Gly Ser Lys
705                 710                 715                 720

Glu Lys Tyr Phe Tyr Ala Lys Ile Tyr Val Asn Lys Gln Arg Gln Thr
                725                 730                 735

Ser Phe Leu Gln Lys Glu Tyr Pro Leu Leu Leu Lys Tyr Leu Lys Leu
                740                 745                 750

Pro Glu Asn Leu Gln Trp Phe Tyr Ile Arg Tyr Lys Asp Asp Gly Lys
            755                 760                 765

Asp Ser Ile Arg Leu Arg Ile Arg Tyr Val Glu Asp Lys Gln Leu Val
    770                 775                 780

Gln Leu Tyr Ser Arg Phe Ile Glu Trp Ala Thr Lys Ala Arg Lys Asn
785                 790                 795                 800

Ile Gln Ile Ser Gly Tyr Glu Ile Ser Glu Tyr Ile Pro Glu Ser Ala
                805                 810                 815

Arg Tyr Gly Gly Lys Lys Tyr Ser Ser Ile Ile His Ser Phe Phe Tyr
                820                 825                 830

Tyr Asp Ser Ile Leu Asp Leu Leu Gln Lys Lys Ala Glu Gln Thr
            835                 840                 845

Ile Glu Val Arg Thr Ser Leu Ser Ile Ile Arg Met Phe Leu Met Met
    850                 855                 860

Lys Leu Ser Leu Gln Asp Gln Gln Lys Leu Ile Lys Asn Leu Phe Asp
```

```
                865                 870                 875                 880
Gly Lys His Lys Leu Lys Tyr Glu Lys Glu Tyr His Asn Ser Ile Ser
                    885                 890                 895

Leu Leu Leu Asp Asn Leu Cys Thr Lys Asn Gln Thr Asp Glu Ala Asp
                900                 905                 910

Ile Phe Cys Val Met Asn Met Lys Lys Ile Thr Glu Lys Ile Ser Ser
            915                 920                 925

Val Leu Lys Gln Lys Asp Leu Thr Thr Asp Trp Gln Arg Ile Leu Gly
        930                 935                 940

Ser Leu Ile His Met Arg Cys Asn Arg Val Tyr Gly Ile Asn Ser Glu
945                 950                 955                 960

Leu Glu Arg Lys Thr Met Phe Ile Val Asp Lys Val Ile Asn Ser Lys
                965                 970                 975

Arg Tyr Thr Asp Met Phe Leu Glu Val Gly Asn Glu Thr Lys
                980                 985                 990

<210> SEQ ID NO 8
<211> LENGTH: 424
<212> TYPE: PRT
<213> ORGANISM: Streptococcus mutans

<400> SEQUENCE: 8

Met Arg Gln Ser Lys Arg Val Glu Lys Ile Lys Asp Ile Leu Thr Glu
1               5                   10                  15

Gln Thr Tyr Leu Phe Asp Tyr Gln Glu Ile Leu Lys Lys Val Ser Gln
                20                  25                  30

Ala Lys Gln Thr Asp Phe Trp Asn Leu Leu Ser Leu Ser Ser Gly Ile
            35                  40                  45

Thr Ser Leu Leu Ile Phe Tyr Gln Tyr Glu Asn Leu Glu Gly Val
        50                  55                  60

Asn Leu Lys Gln Gln Lys Gln Ser Leu Ile Gly Leu Ile Ser His Tyr
65                  70                  75                  80

Ile Asn Gln Ile Ala Glu Lys Ser Ser Leu Phe Asp Gly Leu Ala Gly
                85                  90                  95

Val Gly Phe Ala Ile Asn Tyr Ile Ser Asn Asn Gly Lys Tyr Tyr Gln
                100                 105                 110

Lys Leu Leu Glu Gln Ile Asp Asn Arg Leu Arg Gln Asn Ile Glu Arg
            115                 120                 125

Asn Leu Val Asn Tyr Lys Asn Glu Glu Tyr Ala Asn Pro Met Asn Tyr
        130                 135                 140

Asp Val Val Ser Gly Asn Ala Gly Val Ala Arg Tyr Leu Met Glu Arg
145                 150                 155                 160

Glu Ser Ser Glu Asp Trp Arg Ile Val Glu Met Ile Leu Glu Thr Phe
                165                 170                 175

Tyr Lys Ala Leu Glu Gln Gly Trp Arg Val Gln Ser Lys Tyr Gln Phe
                180                 185                 190

Leu Glu Ser Glu Lys Gln Tyr Tyr Leu Glu Gly Asn Ile Asn Phe Gly
            195                 200                 205

Leu Ala His Gly Ile Leu Gly Pro Ala Thr Ile Met Ala Leu Tyr Gln
        210                 215                 220

Arg Arg Glu Pro Gln Asn Thr Arg Asn Ala Glu Lys Leu Gln Glu Thr
225                 230                 235                 240

Tyr Arg Leu Ile Lys Arg Tyr Ala Gln Val Arg Asp Glu Gly Leu Arg
                245                 250                 255
```

```
Trp Pro Ile Arg Tyr Asp Leu Phe Arg Lys Glu Gly Ser Phe Ile Leu
            260                 265                 270

Arg Asn Gly Trp Cys Tyr Gly Glu Asn Gly Ile Tyr Asn Thr Leu Phe
            275                 280                 285

Leu Met Gly Lys Val Leu Ser Asn Gln Glu Ile Cys Glu Thr Ala Gln
            290                 295                 300

Lys Val Ile Pro Ser Ile Ile Lys Asp Asp Tyr Glu Lys Met Glu Ser
305                 310                 315                 320

Pro Thr Phe Cys His Gly Phe Ala Gly Lys Ala Asn Phe Phe Leu Leu
            325                 330                 335

Gln Tyr Gln Arg Thr Lys Glu Ser Ile Phe Leu Val Lys Ala Glu Glu
            340                 345                 350

Glu Ile Asp Lys Ile Leu Ile Val Tyr Asn Ser Glu Asn Met Phe Gly
            355                 360                 365

Phe Lys Asp Ile Glu Asp Asn Ile Asp Asn Thr Gly Glu Arg Leu Thr
            370                 375                 380

Tyr Trp Asp Asn Phe Gly Leu Leu Ser Gly Thr Val Gly Val Leu Leu
385                 390                 395                 400

Val Leu Met Glu Tyr Cys Asn Ile Val Asn Ala Gly Lys Ile Ala Glu
            405                 410                 415

Trp Asn Lys Ile Phe Leu Leu Thr
            420

<210> SEQ ID NO 9
<211> LENGTH: 188
<212> TYPE: PRT
<213> ORGANISM: Streptococcus mutans

<400> SEQUENCE: 9

Met Glu Glu Gln Asn Ile Glu Lys Lys Ile Leu Leu Cys Leu Thr Gly
1               5                   10                  15

Ser Gly Ala Leu Leu Gly Ile Ala Glu Tyr Ile Thr Phe Leu Thr Val
            20                  25                  30

Arg Phe Lys His Val Arg Val Ile Val Ser Asp Asn Ala Ala Lys Met
            35                  40                  45

Leu Pro Val Ala Ala Ile Thr Gln Leu Cys Glu Lys Val Tyr Thr Asp
            50                  55                  60

Glu Val Ser Phe Thr Asp Lys Gln Lys Asn His Ile Ala Leu Thr Arg
65                  70                  75                  80

Trp Ala Asp Ile Thr Val Val Leu Pro Ala Thr Ala Asn Ile Ile Gly
            85                  90                  95

Lys Val Ala Asn Gly Ile Ala Asp Asn Phe Met Thr Thr Thr Leu Leu
            100                 105                 110

Ser Ser Ser Lys Pro Val Leu Ile Tyr Pro Cys Met Asn Asn Ile Met
            115                 120                 125

Trp Glu Asn Pro Val Val Gln Lys Asn Val Glu Val Leu Ser Gly Thr
            130                 135                 140

Gln Tyr Lys Val Ile Val Gly Gln Glu Ser Glu Ser Phe Glu Leu Ala
145                 150                 155                 160

Ser Gly Lys Met Lys Lys Asn Ile Ala Ile Pro Ser Leu Asp Glu Leu
            165                 170                 175

Gln Arg Val Val Leu Glu Asn Leu Gln Glu Glu Arg
            180                 185

<210> SEQ ID NO 10
```

```
<211> LENGTH: 447
<212> TYPE: PRT
<213> ORGANISM: Streptococcus mutans

<400> SEQUENCE: 10
```

| | | | | | | | | | | | | | | | |
|---|---|---|---|---|---|---|---|---|---|---|---|---|---|---|---|
| Met | Lys | Lys | Lys | Gly | Leu | Leu | Val | Ile | Ile | Phe | Leu | Thr | Phe | Phe | Phe |
| 1 | | | | 5 | | | | | 10 | | | | | 15 | |

| Phe | Tyr | Pro | Lys | Ala | Lys | Ala | Ala | Glu | Tyr | Thr | Ile | Ile | Ser | Asn | Asn |
|---|---|---|---|---|---|---|---|---|---|---|---|---|---|---|---|
| | | | 20 | | | | | 25 | | | | | 30 | | |

| Ser | Glu | Gln | Thr | Val | Asn | Asp | Leu | Asn | Asn | Leu | Gly | Val | Thr | Val | Asn |
|---|---|---|---|---|---|---|---|---|---|---|---|---|---|---|---|
| | | | 35 | | | | | 40 | | | | | 45 | | |

| Ser | His | Ile | Ala | Glu | Ile | Gly | Tyr | Ile | Glu | Ala | Gln | Gly | Asp | Val | Asn |
|---|---|---|---|---|---|---|---|---|---|---|---|---|---|---|---|
| | | | 50 | | | | | 55 | | | | | 60 | | |

| Ile | Asp | Gln | Ile | Lys | Lys | Leu | Ser | Asn | Ile | Gln | Ser | Ile | Gln | Asn | Met |
|---|---|---|---|---|---|---|---|---|---|---|---|---|---|---|---|
| 65 | | | | | 70 | | | | | 75 | | | | | 80 |

| Ala | Asp | Thr | Ser | Gln | Asn | Ile | Thr | Thr | Arg | Val | Pro | Ser | Thr | Tyr | Ile |
|---|---|---|---|---|---|---|---|---|---|---|---|---|---|---|---|
| | | | | 85 | | | | | 90 | | | | | 95 | |

| Asn | Gln | Thr | Ile | Gln | Leu | Pro | Gln | Leu | Phe | Ser | Tyr | Gln | Trp | Asp | Met |
|---|---|---|---|---|---|---|---|---|---|---|---|---|---|---|---|
| | | | 100 | | | | | 105 | | | | | 110 | | |

| Gln | Lys | Ile | Thr | Asn | Asn | Gly | Val | Ser | Tyr | Ser | Leu | Asn | Lys | Glu | Asn |
|---|---|---|---|---|---|---|---|---|---|---|---|---|---|---|---|
| | | | 115 | | | | | 120 | | | | | 125 | | |

| Arg | Lys | Asn | Val | Thr | Val | Ala | Leu | Val | Asp | Ser | Gly | Ile | Asp | Val | Asp |
|---|---|---|---|---|---|---|---|---|---|---|---|---|---|---|---|
| | 130 | | | | | 135 | | | | | 140 | | | | |

| His | Asn | Ala | Phe | Thr | Gly | Met | Ile | Asp | Ser | Arg | Ser | Lys | Asn | Phe | Val |
|---|---|---|---|---|---|---|---|---|---|---|---|---|---|---|---|
| 145 | | | | | 150 | | | | | 155 | | | | | 160 |

| Pro | Ala | Gly | Gly | Tyr | Asp | Asn | Ser | Glu | Ser | Ser | Glu | Thr | Gly | Asn | Ile |
|---|---|---|---|---|---|---|---|---|---|---|---|---|---|---|---|
| | | | | 165 | | | | | 170 | | | | | 175 | |

| Asn | Asp | Ile | Asp | Asp | Lys | Lys | Gly | His | Gly | Thr | Ala | Val | Ala | Gly | Gln |
|---|---|---|---|---|---|---|---|---|---|---|---|---|---|---|---|
| | | | 180 | | | | | 185 | | | | | 190 | | |

| Ile | Ala | Ala | Asn | Gly | Gln | Ile | Phe | Gly | Val | Ser | Pro | Gly | Thr | Asn | Leu |
|---|---|---|---|---|---|---|---|---|---|---|---|---|---|---|---|
| | | | 195 | | | | | 200 | | | | | 205 | | |

| Leu | Ile | Tyr | Arg | Val | Phe | Gly | Lys | Ser | Lys | Ser | Lys | Glu | Cys | Trp | Ile |
|---|---|---|---|---|---|---|---|---|---|---|---|---|---|---|---|
| | 210 | | | | | 215 | | | | | 220 | | | | |

| Leu | Lys | Ala | Ile | Ile | Asp | Ala | Thr | Asn | Asn | Gly | Ala | Asn | Val | Ile | Asn |
|---|---|---|---|---|---|---|---|---|---|---|---|---|---|---|---|
| 225 | | | | | 230 | | | | | 235 | | | | | 240 |

| Leu | Ser | Leu | Gly | Gln | Tyr | Ile | Lys | Ile | Pro | Asn | Gly | Asp | Ile | Trp | Glu |
|---|---|---|---|---|---|---|---|---|---|---|---|---|---|---|---|
| | | | | 245 | | | | | 250 | | | | | 255 | |

| Ser | Ala | Glu | Ala | Leu | Gly | Tyr | Lys | Phe | Ala | Ile | Asp | Tyr | Ala | Thr | Arg |
|---|---|---|---|---|---|---|---|---|---|---|---|---|---|---|---|
| | | | 260 | | | | | 265 | | | | | 270 | | |

| His | Asn | Val | Ile | Val | Val | Ala | Thr | Gly | Asn | Asp | Gly | Leu | Ser | Asp |
|---|---|---|---|---|---|---|---|---|---|---|---|---|---|---|
| | | | 275 | | | | | 280 | | | | | 285 | |

| Asp | Asn | Gly | Glu | Val | Lys | Thr | Tyr | Tyr | Asn | Ser | Gln | His | Ser | Gly | Gln |
|---|---|---|---|---|---|---|---|---|---|---|---|---|---|---|---|
| | 290 | | | | | 295 | | | | | 300 | | | | |

| Asp | Met | Ser | Gln | Asn | Asp | Thr | Val | Glu | Asp | Tyr | Pro | Ser | Val | Leu | Pro |
|---|---|---|---|---|---|---|---|---|---|---|---|---|---|---|---|
| 305 | | | | | 310 | | | | | 315 | | | | | 320 |

| Asn | Ala | Ile | Ala | Val | Gly | Ser | Ser | Asp | Asn | Asn | Gln | Arg | Ser | Ser |
|---|---|---|---|---|---|---|---|---|---|---|---|---|---|---|
| | | | | 325 | | | | | 330 | | | | | 335 |

| Phe | Ser | Asn | Tyr | Tyr | Asn | Gln | Tyr | Gln | Asp | Asn | Phe | Ile | Leu | Ala | Pro |
|---|---|---|---|---|---|---|---|---|---|---|---|---|---|---|---|
| | | | 340 | | | | | 345 | | | | | 350 | | |

| Gly | Gly | Gly | Thr | Thr | Leu | Leu | Asp | Gln | Tyr | Gly | Gln | Glu | Glu | Trp | Tyr |
|---|---|---|---|---|---|---|---|---|---|---|---|---|---|---|---|
| | | | 355 | | | | | 360 | | | | | 365 | | |

| Asn | Gln | Lys | Leu | Phe | Met | Lys | Glu | Gln | Val | Leu | Ser | Thr | Ser | Asn | Asn |
|---|---|---|---|---|---|---|---|---|---|---|---|---|---|---|---|
| | 370 | | | | | 375 | | | | | 380 | | | | |

| Gly | Asn | Tyr | Asp | Tyr | Ala | Asp | Gly | Thr | Ser | Ile | Ser | Thr | Gly | Lys | Val |

-continued

```
                385                 390                 395                 400
Ser Gly Glu Leu Ala Glu Ile Ile Ser Asn Tyr His Leu Gln Gly Asp
                    405                 410                 415

Ser Ser Lys Ala Arg Ser Ile Leu Leu Asn Gln Val Asn Tyr Thr Ser
                    420                 425                 430

Asp Gly Tyr Lys Glu Ile Ser Thr Tyr Lys Ala Leu Arg Gly Tyr
            435                 440                 445

<210> SEQ ID NO 11
<211> LENGTH: 541
<212> TYPE: PRT
<213> ORGANISM: Streptococcus mutans

<400> SEQUENCE: 11

Met Lys Trp Leu Glu Val Leu Gln Ile Ser Lys Lys Glu Lys Ile Leu
1               5                   10                  15

Tyr Leu Ile Gly Cys Ile Phe Ser Ile Met Thr Gly Leu Ile Thr Leu
                20                  25                  30

Arg Ile Thr Tyr Leu Leu Lys Asn Leu Val Asp Ser Lys Ser Ser Phe
            35                  40                  45

Asn Asn Leu Phe Leu Phe Leu Val Leu Gly Leu Val Leu Phe Ile Ile
50                  55                  60

Asp Ala Gly Ser Gln Tyr Leu Ile Ser Leu Ile Gly Asn Gln Val Val
65                  70                  75                  80

Phe Asn Ser Arg Asn Asn Ile Trp Lys Lys Ile Ser Asp Trp Thr Asp
                85                  90                  95

Ser Lys Asp Asp Ser Ser Glu Met Ala Gly His Leu Ile Asn Asp Ser
            100                 105                 110

Glu Leu Ile Glu Asn Phe Ile Ile Ser Thr Ile Pro Gln Ser Ile Asn
        115                 120                 125

Ser Val Ile Val Gly Ser Gly Ser Leu Val Met Leu Phe Val Ile Asn
    130                 135                 140

Ser Lys Met Ser Leu Glu Val Ile Gly Ile Cys Leu Leu Leu Leu Phe
145                 150                 155                 160

Ile Met Gln Pro Phe Ser Arg Ile Leu Ser Lys Ile Ser Lys Arg Ile
                165                 170                 175

Gln Glu Asp Lys Ala Glu Leu Ile Asn Ile Ala Ser Gln Leu Arg Gly
            180                 185                 190

Gln Val Lys Thr Ile Lys Ser Tyr Asn Ala Gln Asp Tyr Ala Phe Gln
        195                 200                 205

Lys Phe Asp Glu Gln Asn Arg Gln Leu Phe Gln Asp Ile Leu Asn Arg
    210                 215                 220

Ile Lys Ile Phe Ser Ile Tyr Ser Pro Phe Leu Asn Ile Leu Ile Leu
225                 230                 235                 240

Phe Met Ile Ile Ile Val Val Trp Leu Gly Asn Thr Glu Val Arg Ser
                245                 250                 255

Gly Asn Leu Thr Val Gly Ser Ala Thr Ile Phe Val Val Tyr Met Thr
            260                 265                 270

Gln Leu Ile Asn Pro Ile Met Gln Leu Ser Gln Leu Val Ala His Met
        275                 280                 285

Gly Met Leu Asn Gly Gly Val Glu Arg Leu Leu Glu Tyr Asn Gln Ala
    290                 295                 300

Ile Pro Glu Lys Asn Gly Ile Lys Lys Ile Asp Glu Ile Ile Asn Ile
305                 310                 315                 320
```

```
Ala Phe Asp Asn Val Ser Phe Ala Tyr Asp Asn Gln Glu Asn Ile Ile
                325                 330                 335

Glu Asn Val Asn Leu Thr Phe Gln Lys Gly Thr Tyr Ile Ser Ile Val
                340                 345                 350

Gly Glu Ser Gly Val Gly Lys Ser Thr Leu Leu Asp Leu Leu Glu His
                355                 360                 365

Asn Tyr Val Pro Ser Lys Gly Arg Ile Leu Ile Asn Gly Ile Asp Leu
                370                 375                 380

Glu Glu Leu Asn Ile Lys Thr Leu Arg Asn Lys Ile Ser Tyr Val Ser
385                 390                 395                 400

Gln Glu Pro Thr Ile Leu Ser Gly Thr Ile Arg Glu Leu Leu Asp Phe
                405                 410                 415

Asn Gln Gln His Thr Glu Thr Ser Leu Trp Asn Val Leu Asp Thr
                420                 425                 430

Val Glu Leu Ser Glu Leu Ile Arg Asn Leu Pro Ala Lys Leu Asp Ser
                435                 440                 445

Lys Val Asp Glu Tyr Gly Gly Asn Leu Ser Gly Gln Met Gln Arg
    450                 455                 460

Ile Ser Leu Ala Arg Gly Leu Leu Lys Ala Gly Asp Val Leu Leu Leu
465                 470                 475                 480

Asp Glu Ser Phe Ala Asn Ile Asp Glu Glu Thr Cys Leu Lys Ile Lys
                485                 490                 495

Leu Lys Ile Ala Ala Tyr Ala Glu Ser His Lys Gln Ile Val Ile Glu
                500                 505                 510

Val Ile His Asn Leu Asn Arg Ile Thr Pro Ser Ser Ile Val Tyr Arg
                515                 520                 525

Leu Ala Asp Lys Lys Leu Glu Ile Leu Arg Ser Gly Phe
                530                 535                 540

<210> SEQ ID NO 12
<211> LENGTH: 233
<212> TYPE: PRT
<213> ORGANISM: Streptococcus mutans

<400> SEQUENCE: 12

Met Asp Tyr Met Leu Glu Thr Lys Asn Leu Thr Lys Gln Phe Gly Lys
1               5                   10                  15

Gln Thr Ala Val Asn Gln Leu Asn Leu Lys Val Glu Arg His Ser Ile
                20                  25                  30

Tyr Gly Leu Leu Gly Pro Asn Gly Ser Gly Lys Ser Thr Thr Leu Lys
                35                  40                  45

Met Ile Thr Gly Met Leu Arg Lys Thr Ser Gly His Ile Leu Ile Asp
        50                  55                  60

Gly His Asp Trp Ser Arg Lys Asp Leu Glu Asn Ile Gly Ala Leu Ile
65                  70                  75                  80

Glu Ser Pro Pro Leu Tyr Glu Asn Leu Thr Ala Arg Glu Asn Leu Lys
                85                  90                  95

Val Arg Thr Leu Met Leu Gly Leu Pro Asp Ser Arg Ile Asp Glu Val
                100                 105                 110

Leu Lys Ile Val Asp Leu Thr Asn Thr Gly Lys Lys Arg Ala Gly Gln
                115                 120                 125

Phe Ser Met Gly Met Lys Gln Arg Leu Gly Ile Ala Ile Ala Leu Leu
        130                 135                 140

Asn Ser Pro Gln Leu Leu Ile Leu Asp Glu Pro Thr Asn Gly Leu Asp
145                 150                 155                 160
```

```
Pro Ile Gly Ile Gln Glu Leu Arg Asn Leu Ile Arg Ser Phe Pro Thr
                165                 170                 175
Gln Gly Ile Thr Val Ile Ile Ser Ser His Ile Leu Ser Glu Ile Gln
            180                 185                 190
Met Thr Ala Asp His Ile Gly Ile Ile Ala Asn Gly Val Leu Gly Tyr
        195                 200                 205
Gln Asp Arg Ile His Gln Asp Glu Asp Leu Glu Lys Leu Phe Thr Asp
    210                 215                 220
Val Val Met Arg Tyr Arg Gly Gly Glu
225                 230
```

<210> SEQ ID NO 13
<211> LENGTH: 251
<212> TYPE: PRT
<213> ORGANISM: Streptococcus mutans

<400> SEQUENCE: 13

```
Met Leu Gly Met Phe Gln Ala Glu Arg Leu Lys Leu Lys Arg Ser Met
1               5                   10                  15
Ala Lys Lys Leu Leu Val Phe Ala Pro Ile Ala Ile Leu Tyr Gly
            20                  25                  30
Phe Ile Ala Pro Val Gly Tyr Leu Val Asn Asn Ala Tyr Asn Trp Trp
        35                  40                  45
Tyr Val Met Ile Phe Pro Gly Leu Leu Thr Leu Phe Ala Ala Leu Ile
    50                  55                  60
Asn Thr Tyr Glu Glu Lys Lys Leu His Tyr Arg Ala Val Phe Pro Leu
65                  70                  75                  80
Pro Ile Ser Leu Arg Lys Phe Trp Phe Glu Lys Ile Phe Ile Thr Val
                85                  90                  95
Tyr Tyr Leu Asn Phe Ser Asn Gly Val Leu Trp Ile Ile Thr Val Leu
            100                 105                 110
Leu Asn Thr Phe Ile Leu Pro Asn Tyr Gly Lys Asp Tyr Thr Tyr Thr
        115                 120                 125
Val Gly Glu Leu Ala Leu Ala Ser Leu Val Ile Ile Val Thr Thr Leu
    130                 135                 140
Trp Gln Ile Pro Phe Cys Leu Trp Leu Thr Lys Arg Ile Gly Phe Thr
145                 150                 155                 160
Ile Thr Leu Ile Ile Asn Leu Met Ser Asn Phe Ile Leu Gly Val Val
                165                 170                 175
Phe Ala Thr Thr Ser Cys Trp Trp Leu Cys Pro Tyr Ser Trp Gly Ile
            180                 185                 190
Arg Leu Met Val Pro Ile Leu Lys Ile Leu Pro Ser Gly Leu Lys Ala
        195                 200                 205
Gly Ile Ala Gly Ala Pro Ser Leu Pro Thr Ser Phe Trp Ser Ile Val
    210                 215                 220
Ile Ser Leu Cys Leu Ala Val Ile Leu Phe Val Ser Leu Thr Val Leu
225                 230                 235                 240
Ser Ala Ser Trp Phe Glu Lys Gln Glu Val Lys
                245                 250
```

<210> SEQ ID NO 14
<211> LENGTH: 246
<212> TYPE: PRT
<213> ORGANISM: Streptococcus mutans

<400> SEQUENCE: 14

```
Met Ile Asp Leu Leu Lys Ala Glu Asn Val Lys Tyr Arg His Thr Phe
1               5                   10                  15

Leu Pro Trp Leu His Leu Ile Leu Pro Val Thr Thr Ala Ile Val Val
                20                  25                  30

Ile Val Tyr Gly Leu Met Thr Pro Thr His Ser Trp Ala Asp Ile Thr
            35                  40                  45

Gly Gly Tyr Leu Glu Leu Leu Gly Ile Ser Phe Pro Ile Val Ile Ala
        50                  55                  60

Val Ile Cys Gly Lys Ser Val Gly Leu Glu Val Glu Ala Gly Gln Phe
65                  70                  75                  80

Gln Val Met Leu Ala Ile Lys Gln Arg Asn Leu Ile Phe Cys Ile Lys
                85                  90                  95

Leu Leu Asn Leu Leu Ile Leu Glu Leu Phe Ser Thr Leu Leu Ala Ile
                100                 105                 110

Gly Ile Tyr Gly Leu Ile Tyr Gln Leu Ser Asn Lys His Leu Ile Phe
            115                 120                 125

Tyr Gly Tyr Ala Val Ile Leu Leu Thr Ala Ser Met Leu Ile Leu Tyr
        130                 135                 140

Leu Ile His Leu Val Val Val Phe Leu Phe Gly Asn Ser Ala Asn Ile
145                 150                 155                 160

Gly Leu Gly Ile Ala Glu Ser Leu Leu Ser Ala Leu Leu Leu Thr Gly
                165                 170                 175

Leu Gly Asp Gly Ile Trp Gln Phe Ile Pro Cys Ala Trp Gly Thr Arg
                180                 185                 190

Leu Met Gly Thr Leu Ile Asn Leu Trp Tyr Tyr Ser Gly His Ser Leu
            195                 200                 205

Phe Phe Lys Gln Gln Leu Leu Ile Trp Leu Glu Val Ala Val Pro Leu
        210                 215                 220

Thr Leu Met Ala Leu Ile Leu Ser Ile Ile Trp Phe Asp Arg Trp Gln
225                 230                 235                 240

Gly Arg Ser Ser Asp Glu
                245

<210> SEQ ID NO 15
<211> LENGTH: 246
<212> TYPE: PRT
<213> ORGANISM: Streptococcus mutans

<400> SEQUENCE: 15

Met Thr Tyr Ile Gly Val Ser His Leu Lys Lys Val Tyr Lys Thr Gln
1               5                   10                  15

Glu Gly Leu Thr Asn Glu Ala Leu Lys Asp Ile Thr Phe Ser Val Gln
                20                  25                  30

Glu Gly Glu Phe Ile Ala Ile Met Gly Glu Ser Gly Ser Gly Lys Ser
            35                  40                  45

Thr Leu Leu Asn Ile Leu Ala Cys Met Asp Tyr Pro Ser Ser Gly His
        50                  55                  60

Ile Ile Phe Asn Asn Tyr Gln Leu Glu Lys Val Lys Asp Glu Glu Ala
65                  70                  75                  80

Ala Val Phe Arg Ser Arg His Ile Gly Phe Ile Phe Gln Asn Phe Asn
                85                  90                  95

Leu Leu Asn Ile Phe Asn Asn Lys Asp Asn Leu Leu Ile Pro Val Ile
                100                 105                 110

Ile Ser Gly Ser Lys Val Asn Ser Tyr Glu Lys Arg Leu Arg Asp Leu
```

```
            115                 120                 125
Ala Ala Val Val Gly Ile Glu Ser Leu Leu Ser Lys Tyr Pro Tyr Glu
130                 135                 140

Leu Ser Gly Gly Gln Gln Gln Arg Leu Ala Ile Ala Arg Ala Leu Ile
145                 150                 155                 160

Met Asn Pro Asp Leu Ile Leu Ala Asp Glu Pro Thr Gly Gln Leu Asp
                165                 170                 175

Ser Lys Thr Ser Gln Arg Ile Leu Asn Leu Leu Ser Asn Ile Asn Ala
                180                 185                 190

Lys Arg Lys Thr Ile Leu Met Val Thr His Ser Pro Lys Ala Ala Ser
                195                 200                 205

Tyr Ala Asn Arg Val Leu Phe Ile Lys Asp Gly Val Ile Phe Asn Gln
210                 215                 220

Leu Val Arg Gly Cys Lys Ser Arg Glu Gly Phe Leu Asp Gln Ile Ile
225                 230                 235                 240

Met Ala Gln Ala Ser Leu
                245

<210> SEQ ID NO 16
<211> LENGTH: 640
<212> TYPE: PRT
<213> ORGANISM: Streptococcus mutans

<400> SEQUENCE: 16

Met Phe Leu Pro Lys Ile Ser Phe His Asn Leu Ile Val Asn Lys Ser
1               5                   10                  15

Leu Thr Leu Pro Tyr Phe Ala Ile Met Thr Ile Phe Ser Gly Phe Asn
                20                  25                  30

Tyr Val Leu Ile Asn Phe Leu Thr Asn Pro Ser Phe Tyr Asn Ile Pro
            35                  40                  45

Thr Ala Arg Ile Leu Ile Asp Ile Leu Ile Phe Gly Phe Ile Leu Ile
        50                  55                  60

Ser Leu Leu Met Leu Leu Tyr Gly Arg Tyr Ala Asn Arg Phe Ile Ser
65                  70                  75                  80

Asp Glu Arg Asn Ser Asn Met Gly Ile Phe Leu Met Leu Gly Met Gly
                85                  90                  95

Lys Lys Gln Leu Leu Lys Ile Ile Tyr Leu Glu Lys Leu Tyr Leu Phe
                100                 105                 110

Thr Gly Thr Phe Phe Gly Gly Leu Ile Phe Gly Phe Val Tyr Ser Lys
                115                 120                 125

Ile Phe Phe Leu Phe Ile Arg Asn Leu Ile Val Ile Gly Asp Val Arg
130                 135                 140

Glu Gln Tyr Ser Leu Thr Ala Ile Ser Trp Leu Leu Ile Leu Thr Phe
145                 150                 155                 160

Phe Ile Tyr Phe Ile Ile Tyr Leu Ser Glu Tyr Arg Leu Leu Lys Arg
                165                 170                 175

Gln Ser Ile Thr Val Ile Phe Asn Ser Lys Ala Lys Arg Asp Asn Pro
                180                 185                 190

Arg Lys Thr Ser Val Phe Val Gly Leu Phe Gly Leu Phe Ala Leu Leu
                195                 200                 205

Met Gly Tyr His Phe Ala Leu Thr Ser Pro Asn Val Thr Thr Ser Phe
                210                 215                 220

Ser Arg Phe Ile Tyr Ala Ala Cys Leu Val Thr Leu Gly Ile Phe Cys
225                 230                 235                 240
```

Thr Phe Ser Ser Gly Val Ile Met Leu Leu Thr Val Ile Lys Lys Arg
            245                 250                 255

Arg Ala Ile Tyr Tyr Asn Gln Arg Arg Phe Val Val Ile Ala Ser Leu
            260                 265                 270

Phe His Arg Ile Arg Ser Asn Ala Leu Ser Leu Ala Thr Ile Cys Ile
            275                 280                 285

Phe Ser Thr Ala Thr Leu Val Ser Leu Ser Val Leu Ala Ser Leu Tyr
290                 295                 300

Leu Ala Lys Asp Asn Met Val Arg Leu Ser Ser Pro Arg Asp Val Thr
305                 310                 315                 320

Val Leu Ser Thr Thr Asp Ile Glu Pro Asn Leu Met Asp Ile Ala Thr
                325                 330                 335

Lys Asn His Val Thr Leu Thr Asn Arg Gln Asn Leu Lys Val Ser Gln
            340                 345                 350

Ser Val Tyr Gly Asn Ile Lys Gly Ser His Leu Ser Val Asp Pro Asn
            355                 360                 365

Gly Gly Met Ala Asn Asp Tyr Gln Ile Thr Val Ile Ser Leu Asp Ser
370                 375                 380

Phe Asn Ala Ser Asn Asn Thr His Tyr Arg Leu Lys Asn His Glu Ile
385                 390                 395                 400

Leu Thr Tyr Val Ser Asn Gly Ala Ala Pro Ser Ser Tyr Thr Thr
                405                 410                 415

Asn Gly Val Lys Leu Thr Asn Val Lys Gln Ile Lys Arg Ile Asn Phe
            420                 425                 430

Ile Phe Ser Pro Leu Arg Ser Met Gln Pro Asn Phe Phe Ile Ile Thr
                435                 440                 445

Asp Asn Arg Glu Ile Ile Gln Thr Ile Leu Lys Glu Glu Leu Thr Trp
450                 455                 460

Gly Thr Met Ala Gly Tyr His Val Lys Gly Lys Lys Met Asn Gln Lys
465                 470                 475                 480

Asp Phe Tyr Asp Glu Leu Glu Thr Thr Asn Phe Arg Gln Phe Ser Ala
                485                 490                 495

Asn Val Val Ser Ile Arg Gln Val Lys Ser Met Phe Asn Ala Leu Phe
            500                 505                 510

Gly Gly Leu Leu Phe Val Gly Ile Ile Phe Gly Thr Ile Phe Ala Ile
            515                 520                 525

Leu Thr Ala Ile Thr Ile Tyr Tyr Gln Gln Leu Ser Glu Gly Ile Arg
530                 535                 540

Asp Arg Asp Asp Tyr Lys Ala Met Ile Lys Leu Gly Met Thr Asn Lys
545                 550                 555                 560

Thr Ile Gln Asp Ser Ile Lys Val Gln Ile Asn Phe Val Phe Ile Leu
                565                 570                 575

Pro Ile Ala Phe Ala Leu Leu Asn Leu Ile Phe Ala Leu Pro Ile Leu
            580                 585                 590

Tyr Lys Ile Met Thr Thr Phe Gly Phe Asn Asp Ala Gly Leu Phe Leu
            595                 600                 605

Arg Ala Val Gly Thr Cys Leu Ile Val Tyr Leu Phe Phe Tyr Trp Phe
610                 615                 620

Ile Cys His Cys Thr Ser Lys Leu Tyr Tyr Arg Leu Ile Ser Lys Lys
625                 630                 635                 640

<210> SEQ ID NO 17
<211> LENGTH: 118
<212> TYPE: PRT

```
<213> ORGANISM: Streptococcus mutans

<400> SEQUENCE: 17

Met Arg Ile Val Ser Ser Leu Val Ser Leu Leu Thr Ile Phe Trp
1               5                   10                  15

Ile Phe Ala Ile Ala Phe Ile Pro Ile Gly Asp Gln Asn Ser Phe Asn
            20                  25                  30

Lys Pro Glu Met Trp Phe Phe Val Phe Phe Ala Ile Ile Ile Tyr Ser
                35                  40                  45

Ile Val Ile Ile Ser Asp Tyr Tyr Leu Lys Ser Phe Asn Leu Leu Lys
        50                  55                  60

Val Tyr Gln Ile Leu Val Leu Phe Ile Ser Ile Leu Cys Ala Leu Cys
65                      70                  75                  80

Gly Leu Ser Leu Thr Ala Leu Gly Leu Lys Val Phe Thr Leu Ala Ile
                85                  90                  95

Gly Ile Val Ser Leu Val Asn Thr Ile Ile Tyr Phe Phe Phe Ala Asn
            100                 105                 110

Lys Lys Asp Asn Val Glu
        115
```

MUTACIN I BIOSYNTHESIS GENES AND PROTEINS

GRANT REFERENCE

The subject invention was made with government support under a grant from the National Institutes of Health (NIH RO 1 DE09082). The government has certain rights in the invention.

FIELD OF THE INVENTION

The invention relates to polypeptide antibiotics and to the identification of genetic loci associated with expression of the antibiotics. The invention particularly describes a purified lanthionine-containing antimicrobial agent, DNA encoding the protein, and methods and compositions for treatments employing the antibiotic.

BACKGROUND OF THE INVENTION

Several species of bacteria inhabit the human oral cavity; among them *Streptococcus mutans* is considered a major etiologic agent responsible for dental caries. Loesche (1986) *Microbiol. Rev.* 50:353–380. Previous studies showed a certain percentage of clinical isolates of *S. mutans* producing antimicrobial substances called mutacins. Caufield et al. (1985) *Infect. Immun.* 48:51–56; Hamada et al. (1975) *Arch. Oral Biol.* 20:641–648. Mutacins are active against closely related species as well as a surprisingly wide spectrum of other Gram-positive bacteria. Parrot et al. (1990) *Can. J Microbiol.* 36:123–130. The ability to produce mutacins, combined with lactic acid production by *S. mutans* may contribute to the pathogenesis of these bacteria. Kleinberg, p. 605–624, in W. A. Nolte (ed.), Oral microbiology, The C.V. Mosby Company, St. Louis. Production of mutacins by *S. mutans* and other oral streptococci may also play a protective role to the host against pathogens such as Group A streptococci and *Streptococcus pneumoniae*. In this respect, mutacins may serve as antimicrobial agents in the future.

Lantibiotics are lanthionine-containing small peptide antibiotics that are produced by gram-positive bacteria. Jung (ed.), p. 1–34, in G. Jung and H. G. Sahl (ed.), Nisin and novel lantibiotics, ESCOM Sci. Publ., Leiden; Sahl et al. (1995) *Eur. J. Biochem.* 230:827–853. The lantibiotics are ribosomally synthesized and post-translationally modified. The modification reactions include dehydration of serine and threonine residues and the addition of thiol groups from cycteine residues to the double bound to form lanthionines and β-methyllanthiones, respectively. Some dehydrated serine or threonine may remain as such in the mature lantibiotic molecule.

Based on the secondary structures, Jung assigned lantibiotics into two classes, Type-A (linear) and Type-B (globular). Jung (ed.), p. 1–34, in G. Jung and H. G. Sahl (ed.), Nisin and novel lantibiotics, ESCOM Sci. Publ., Leiden. de Vos et al. ((1995) *Molecular Microbiol.* 17:427–437) and Sahl and Bierbaum (Sahl et al. (1998) *Annu. Rev. Microbiol.* 52:41–79) further divided each class into subgroups according to their primary peptide sequences. Thus, subgroup AI contains the nisin-like lantibiotics with nisin, subtilin, epidermin and pep5 as the most thoroughly characterized members. Allgaier et al. (1986) *Eur. J. Biochem.* 160:9–22; Gross et al. (1968) *FEBS Lett* 2:61–64; Gross et al. (1971) *J Am. Chem. Soc.* 93:4634–4635; Kaletta et al. (1989) *Arch. Microbiol.* 152:16–19; Weil et al. (1990) *Eur. J. Biochem.* 194:217–223.

Subgroup AII consists of lacticin 481, SA-FF22, salivaricin and variacin. Hynes et al. (1993) *Appl. Environ. Microbiol.* 59:1969–1971; Piard et al. (1993) *J. Biol. Chem.* 268:16361–16368; Pridmore et al. (1996) *Appl. Environ, Microbiol.* 62:1799–1802; Ross et al. (1993) *Appl. Environ. Microbiol.* 59:2014–2021. The genes responsible for the biosynthesis of the lantibiotics are organized in operon-like structures. The biosynthesis locus of all members in the subgroup AI lantibiotics consists of lanA, the structural gene for the lantibiotic; lanB and lanC, the modifying enzyme genes for post-translational modification of the preprolantibiotic; lanP, the protease gene for processing of the prelantibiotic; and lanT, the ABC transporter for secretion of the lantibiotic. In addition, epidermin and gallidennin have an extra gene, lanD, which is responsible for the C-terminal oxidative decarboxylation of the lantibiotic. Kupke et al. (1994) *J. Biol. Chem.* 269:5653–5659; Kupke et al. (1995) *J. Biol Chem.* 270:11282–89. In comparison, subgroup AII lantibiotics have simpler genomic organizations. In subgroup AII, lanB and lanC are combined into one gene, lanM, and lanP and lanT are combined into lanT. Chen et al. (1999) *Appl. Environ. Microbiol.* 65:1356–1360; Qi et al. (1999) *Appl Environ. Microbiol* 65:652–658; Rince et al. (1994) *Appl. Environ. Microbiol.* 60:1652–1657. All lantibiotic loci also contain a set of immunity genes, which are responsible for self-protection of the producer strains. Saris et al. (1996) *Antonie van Leeuwenhoek* 69:151–159. Moreover, the expression of the lantibiotic genes is usually regulated either by a single transcription regulator (Peschel et al. (1993) *Mol. Microbiol.* 9:31–39; Qi et al. (1999) *Appl. Environ. Microbiol.* 65:652–658) or by a two-component signal transduction system (de Ruyter et al. (1996) *J. Bacteriol.* 178:3434–3439; Klein et al. (1993) *Appl. Environ. Microbiol.* 59:296–303; Kuipers et al. (1995) J. Biol. Chem. 270:27295–27304).

Previously, the isolation, biochemical and genetic characterizations of mutacin II, produced by a group II strain of the oral bacteria *Streptococcus mutans* was reported. Chen et al. (1999) *Appl Environ. Microbiol.* 65:1356–1360; Novak et al. (1994) *J. Bacteriol.* 176:4316–4320; Novak et al. (1996) *Anal Biochem.* 236:358–360; Qi et al. (1999) *Appl. Environ. Microbiol.* 65:652–658. Mutacin II belongs to subgroup AII in the lantibiotic family. Recently, the isolation and genetic characterization of mutacin III from the group III S. mutans strain UA787 was reported. Qi et al. (1999) *Appl. Environ. Microbiol.* 65:3880–3887. The mature mutacin III is twenty-two amino acids in size, and shows striking similarity with another lantibiotic, epidermin, produced by *Staphylococcus epidermidis*. Allgaier et al. (1986) *Eur. J. Biochem.* 160:9–22. The mutacin III biosynthesis gene locus consists of eight genes in the order of mutR, -A, -A'; -B, -C, -D, -P, and T. The genomic organization and primary sequence of mutacin III places it in subgroup AI with epidermin and galliderniin as its closest neighbors. Applicants disclosed herein the biochemical and genetic characterization of mutacin I. Comparison of the biosynthesis genes between mutacin I and mutacin III reveal striking similarities as well as important differences.

The cloning and sequencing of the novel mutacin I biosynthetic genes by using information from the conserved sequence derived from several other lantibiotics, and the isolation and purification of mutacin I is disclosed herein and provides a novel group of antibiotics which can be utilized as anti-microbial agents against, for example, presently antibiotic resistant microorganisms.

SUMMARY OF THE INVENTION

According to the present invention, an isolated and purified DNA sequence which encodes a lantibiotic, mutacin I, is disclosed. The nucleic acid sequence is set forth in SEQ ID No: 1 and the amino acid sequence is set forth in SEQ ID No: 2. Also disclosed are pharmaceutical compositions containing mutacin I and methods for their use.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended Figures. These Figures form a part of the specification. It is to be noted, however, that the appended Figures illustrate preferred embodiments of the invention and therefore are not to be considered limiting in their scope.

FIGS. 1A–1C. (A) The mutacin III biosynthesis genes. The orientation of the genes and their relative sizes are shown. mutA is the structural gene for prepromutacin I, and mutA' has no known function at present. mutB and -C encode the enzymes for dehydration and thioether bridge formation of premutacin I. mutD encodes a flavoprotein possibly responsible for oxidative decarboxylation of the C-terminal cycteine in premutacin I. mutP and -T code for the protease and ABC transporter, respectively, which are responsible for the processing and transportation of premutacin I. (B) Similarity between MutA and MutA'. The middle row shows the identical amino acids and the conserved changes (+). Arrowhead indicates the processing site in MutA. The leader peptide and the mature peptide moieties were determined based on MutA. (C) Effects of mutA and mutA' mutations on mutacin I production. Cells from an overnight culture plate were stabbed on TH agar plate and incubated at 37° C. for twenty-four hours. The plate was heated at 80° C. for one hour to kill the producing bacteria, then an overnight culture of the indicator strain NY101 was overlaid on top of the plate. The plate was inspected after an overnight incubation at 37° C.

DETAILED DESCRIPTION OF THE INVENTION

Figures 2, 4B:
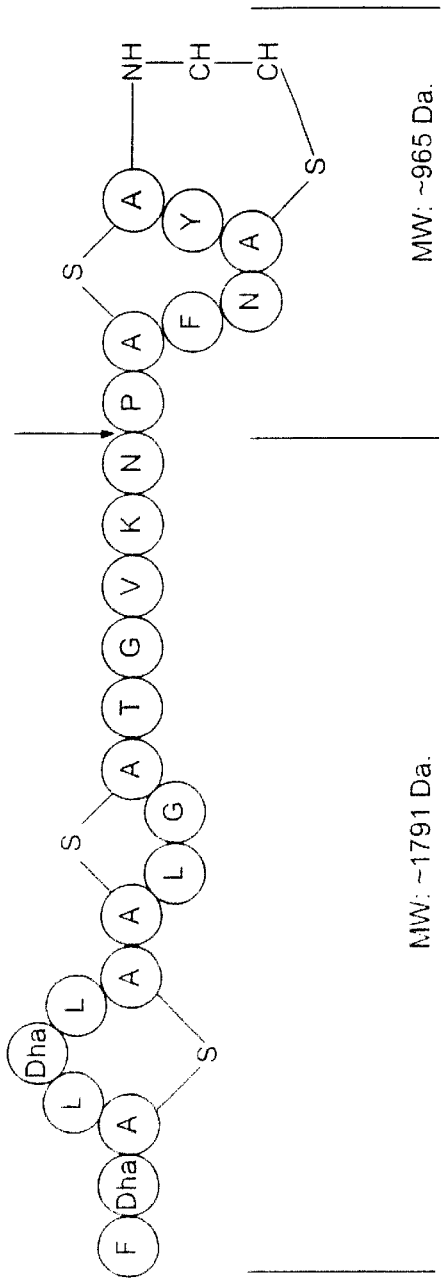
FIG. 2. Similarity between the mutacin I and mutacin III structural gene. The prepropeptides of mutacin I and mutacin III are compared using the sequence of preepidermin as a reference. The identical amino acids shared by all three lantibiotics are labeled with gray boxes, and the amino acids shared by any of two lantibiotics are labeled with an open box. The conserved sequence FNLD, which is shared by all lantibiotics in subgroup AI (29) is underlined. Brackets indicate the pairs of amino acid residues involved with thioether bridge formation in epidermin (1).
FIGS. 4A–4C. Biochemical characterization of mutacin I. (A) EIMS analysis of the ethanethiol-derivatized mutacin I. Peaks 1 and 2 are the doubly-charged molecule of 1791 Da and 1774 Da, respectively. The 1774-Da molecule may be a deaminated form of the 1792 Da molecule. Peak 3 may be a deaminated form of peak 4, both of which are singly charged. Peak 5 and peak 6 are triply-charged and doubly-charged molecule of 2719 Da, respectively. Peak 7 is a doubly-charged molecule of 2736 Da, which gives rise to the deaminated form of 2719 Da (peaks 5 and 6). Peak 8 is a singly-charged, deaminated form of peak 9, which has a molecular mass of 1793 Da. The expected molecular mass of mutacin I after insertion of six molecules of ethanethiol is 2736 Da (2364+62×6), which correlated very well with the measured mass of 2736 as shown by peak 7. Addition of the two molecular masses of 1791 (peak 1) and 965 (peak 4) results in a molecular mass of 2756 Da, which would correlate well with the intact modified mutacin I of 2736 Da plus one molecule of $H_2O$ (from breakage of the molecule). (B) Proposed structure of mutacin I based on the data presented in (A) and in FIG. 2. Arrowhead indicates the position where the peptide bound is broken in the ethanethiol-modified mutacin I. The calculated molecular mass for each fragment is labeled. (C) EIMS analysis of mutacin III derivatized with ethanethiol under the same conditions as for mutacin I. The expected molecular mass for fully derived mutacin II is 2636 (see Table 1), and the measured molecular mass is 2638 from the doubly and triply charged peaks (peaks 2 and 3). The 2620-Da molecule as shown by peaks 1 and 4 are probably the deaminated form of the 2638-Da molecule. The 2576-Da molecule as shown in peak 5 resulted from addition of five molecules of ethanethiol (see Table 1).

The present invention provides an isolated and purified DNA sequence (SEQ ID No: 1) encoding for a novel lantibiotic, mutacin I, that has been isolated and characterized from *Streptococcus mutans* CH43.

Further, the present invention provides the isolated and purified DNA sequence for mutacin I designated as mutA (SEQ ID No: 1) and polymorphisms thereof specific for mutacin I.

By "isolated" it is meant separated from other nucleic acids found in bacteria. By "specific" is meant an isolated sequence which encodes the protein mutacin I.

Further, the present invention provides the amino acid sequence of the mutacin I structural protein SEQ ID No: 2, designated MutA and also referred to herein as mutacin I, functional variants thereof. The mutacin I protein has a molecular weight of approximately 2364 Da and is comprised of twenty-four amino acids in its mature form.

Modification to the nucleic acids of the present invention are also contemplated as long as the essential structure and function of the polypeptide encoded by the nucleic acids are maintained. Likewise, fragments used as primers or probes can have substitutions as long as enough complementary bases exist for selective, specific hybridization with high stringency.

Polymorphisms are variants in the gene sequence. They can be sequence shifts found between various bacterial strains and isolates which, while having a different sequence, produce functionally equivalent gene products. Polymorphisms also encompass variations which can be classified as alleles and/or mutations which can produce gene products which may have an altered function. Polymorphisms also encompass variations which can be classified as alleles and/or mutations which either produce no gene product, an inactive gene product, or increased levels of gene product.

The present invention also includes vectors including the mutacin I genes disposed therein. Such vectors are known or can be constructed by those skilled in the art and should contain all expression elements necessary to achieve the desired transcription of the sequences. Other beneficial characteristics can also be contained within the vectors such as mechanisms for recovery of the nucleic acids in a different form. Phagemids are a specific example of such beneficial vectors because they can be used either as plasmids or as bacteriophage vectors. Examples of other vectors include viruses such as bacteriophages, baculoviruses, and retroviruses, DNA viruses, cosmids, plasmids, liposomes, and other recombination vectors. The vectors can also contain elements for use in either prokaryotic or eukaryotic host systems. One of ordinary skill in the art will know which host systems are compatible with a particular vector.

The vectors can be introduced into cells or tissues by any one of a variety of known methods within the art. Such methods can be found generally described in Sambrook et al., *Molecular Cloning. A Laboratory Manual*, Cold Springs Harbor Laboratory, New York (1989, 1992) and Ausubel et al., *Current Protocols in Molecular Biology*, John Wiley and Sons, Baltimore, Md. (1989); Chang et al., *Somatic Gene Therapy*, CRC Press, Ann Arbor, Mich. (1995); Vega et al., *Gene Targeting*, CRC Press, Ann Arbor, Mich. (1995); *Vectors: A Survey of Molecular Cloning Vectors and Their Uses*, Butterworths, Boston, Mass. (1988); and Gilboa et al. (1986) and include, for example, stable or transient transfection, lipofection, electroporation and infection with recombinant viral vectors. Introduction of nucleic acids by infection offer several advantages over other listed methods. Higher efficiencies can be obtained due to their infectious nature. Moreover, viruses are very specialized and typically infect and propagate in specific cell types. Thus, their natural specificity can be used to target the vectors to specific cell types in vivo or within a tissue or mixed culture of cells. The viral vectors can also be modified with specific receptors or ligands to alter target specificity through receptor mediated events.

The above discussion provides a factual basis for the preparation and use of mutacin I. The methods used with and the utility of the present invention can be shown by the following non-restrictive examples and Figures.

DNA segments encoding a mutacin gene can be introduced into recombinant host cells and employed for expressing a mutacin I protein or peptide. The introduction of the mutacin I expressing DNA can be accomplished, for example, by the introduction of an organism transformed with the mutacin encoding DNA to act as a probiotic and produce the mutacin I in situ to protect against pathogens or other undesirable organisms. Alternatively, through the application of genetic engineering techniques, subportions or derivatives of selected mutacin I genes can be employed. Equally, through the application of site-directed mutagenesis techniques, one may re-engineer DNA segments of the present invention to alter the coding sequence, e.g., to introduce improvements to the antibiotic actions of the resultant protein or to test such mutants in order to examine their structure-function relationships at the molecular level. Where desired, one may also prepare fusion peptides, e.g., where the mutacin I coding regions are aligned within the same expression unit with other proteins or peptides having desired functions, such as for immunodetection purposes (e.g., enzyme label coding regions).

Pharmaceutical Compositions and Formulations

Because of the broad spectrum of activity of mutacin I against a variety of microorganisms, mutacin I can be employed to treat multiple drug resistant bacteria such as certain strains of *S. aureus* which are known to be multiple drug resistant.

Pharmaceutical compositions comprising the disclosed mutacins may be orally administered, for example, with an inert diluent or with an assimilable edible carrier or they may be enclosed in hard or soft shell gelatin capsules or they may be compressed into tablets or may be incorporated directly with the food of the diet.

A therapeutically effective amount is an amount of mutacin I polypeptide, the pharmaceutically acceptable salts, esters, amides, and prodrugs thereof, that when administered to a patient or subject, ameliorates a symptom of the condition or disorder.

The compounds of the present invention can be administered to a patient either alone or as part of a pharmaceutical composition.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis, the polypeptide may be incorporated with excipients and used in the form of non-ingestible mouthwashes, dentifrices or chewing-type gums. A mouthwash may be prepared incorporating the active ingredient in the required amount in an appropriate solvent, such as a sodium borate solution Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compounds sucrose as a sweetening agent, methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally, e.g., formulated for intravenous, intramuscular, or subcutaneous injection. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

Intravascular devices, such as catheters, have become indispensable tools in the care of seriously ill patients. It is estimated that in the United States alone, 150 million catheters are purchased each year. However, due to the morbidity and mortality resulting from catheter-related infections and the high cost of managing such complications, the benefit derived from these devices may be offset. It has been shown that bloodstream infection due to the use of intravascular catheters (IVC) increased dramatically during the last ten years. From 1975 to 1977, an estimated 3% infection occurred among IVC users, while in 1992 to 1993, this rate increased to 19%. The death rate from such infection is ~8000 to 16000 per year, exceeding the death rate for AIDS. The cost for treating IVC-related infections is ~132 to 1600 million per year.

Most infections came from the human skin and the hub of the catheter. Among the infectious bacteria, 40% are coagulase-negative staphylococci, such as *S. epidermidis*, and 14% are coagulase-positive *S. aureus*. The remaining are mostly other gram-positive bacteria such as bacilli and enterococci.

Prophylactic methods have been developed to prevent IVC-related infections. The first line of treatment is to sterilize the insertion site with iodine and 70% ethanol. However, compliance with the written protocol is low; only 23% operations follow the protocol. Another preventative measure is the use of catheters impregnated with antibiotics or antiseptic agents such as chlorhexidine and silver sulfadiazine. In clinical trials, mixed results were obtained using such catheters. In addition to the problem of drug resistance by the infecting bacteria, the antibiotics coating the catheters can also be washed away by body fluid, as the attachment of antibiotics to the catheter surface is mainly through ionic interactions.

Because of the urgency to solve the problem of IVC-related infection and the growing market for development of catheters resistant to bacterial attachment on the surface thereof, mutacins are an excellent choice for prevention of IVC-related infections. Mutacin I has the following advantages over conventional antimicrobial agents: 1) it has a wide spectrum of antimicrobial activity against a wide range of gram-positive bacteria including the multidrug-resistant Staphylococci and Enterococci, the major culprits of IVC-related infections; 2) due to its unique mode of action against the sensitive bacteria, resistance to mutacin has not been observed; 3) mutacin is highly thermostable and works in a wide range of pH which makes it suitable for use in a wide range of conditions; 4) its hydrophobic nature can be advantageous for coating the surface of catheters and preventing adhesion of bacteria to the surface; and 5) because it is produced by a normal member of the human oral biota, it is unlikely to elicit immune response from the patient or has any toxicity to the host.

Active mutacin I compound can be coated onto intravascular devices and/or linked to polymers used in the manufacture of these devices to be used to prevent infection caused by intravascular devices. The mutacin I compounds of the present invention can be utilized alone in combination with at least one other entity, such as linked to a polymer, for the prevention or reduction of infection associated with a variety of medical devices such as indwelling tubes or catheters, artificial valves, pacemakers, implantable devices, etc., by incorporating, coating, or otherwise combining the active mutacin I compounds with the materials comprising the patient contact portions of the medical devices. The polymer can be a hydrophobic material or matrix that can be attached to an indwelling device such as a catheter through hydrophobic bonding or can be tethered to the indwelling device through a molecular linker. The incorporation and/or combination of the active mutacin I compounds may be accomplished by coating the medical devices with active mutacin I compounds or by incorporating the active mutacin I compounds into the structure of the medical device. Because the mutacin I compounds of the present invention are very heat stable, they are able to withstand the conditions associated with their incorporation into the medical devices. By combining and/or incorporating the active mutacin I compounds of the present invention into medical devices, both active and passive infection control can be achieved at sites or for uses, which, in many instances, are highly susceptible or vulnerable to infection.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Barge et al., "Pharmaceutical Salts," *J. Pharm. Sci.,* 1977, 66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines, the amine may also be in the form of a 5- or 6-membered heterocycle containing one nitrogen atom. Amides derived from ammonia, $C_1$–$C_3$ alkyl primary amines, and $C_1$–$C_2$ dialkyl secondary amines are preferred. Amides of the compounds of the invention may be prepared according to conventional methods.

The term "prodrug" refers to compounds that are rapidly transformed in vivo to yield the parent compounds of the above formula, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

The compounds of the present invention can be administered to a patient at various dosage. For example, the dosage can depend on a number of factors including the requirements of the patient, the severity of the condition being treated, and the pharmacological activity of the compound being used. The determination of optimum dosages for a particular patient is well known to those skilled in the art.

EXAMPLES

Materials and Methods

Bacterial Strains and Media

The group I *S. mutans* strain CH43 originated from a Chinese school child as part of a natural history study of human caries. Strain CH43 contains a cryptic plasmid similar to other 5.6-kb plasmids within the *S. mutans* Group I strains. *S. sanguis* strain NY101 was used as the indicator for mutacin activity assays. CH43 and NY101 were grown on Todd-Hewitt (TH) plate with 1.6% agar (Difco Laboratories, Detroit, Mich.) unless indicated otherwise.

Cloning and Sequencing of the Mutacin I Biosynthetic Genes

Cloning and sequencing of the mutacin I biosynthesis genes were performed exactly as described previously. Qi et al. (1999) *Appl Environ. Microbiol.* 65: in press.

Insertional Inactivation

The mutA and mutA' genes were inactivated separately by insertion of a kanamycin-resistant gene cassette exactly as described for mutacin III. Qi et al. (1999) *Appl. Environ. Microbiol.* 65:625–658.

Isolation and Purification of Mutacin I

For mutacin production, CH43 was grown on TH/agar plate for one day under anaerobic conditions. The cells were then spread on a PHWP membrane with 0.3 μm pore size (Millipore Corp., Bedford, Mass.) on top of a TH plate containing 0.3% agarose. The plate was incubated at 37° C. for two days anaerobically. The membrane was transferred to a new plate for continued incubation every two days, and the old plate was frozen at −70° C. For mutacin isolation, the plates were thawed quickly in a 60° C. water bath. The liquid medium was separated from the agarose debris by centrifugation and the supernatant was passed through a membrane with 0.45 μm pore size. Mutacin I was extracted with an equal volume of chloroform. Novak et al. (1994) *J. Bacteriol.* 176:4316–4320. The precipitate was dried under a stream of air and washed once with double-distilled $H_2O$ (dd$H_2O$). The water-insoluable material (crude extract) was dissolved in 6 M urea and tested for antimicrobial activity by a plate assay after a serial dilution with dd$H_2O$. One arbitrary unit of activity (AU) was defined as the highest dilution that showed a clear zone of inhibition of the indicator strain NY101.

For purification, the crude extract of mutacin I was applied to a Source 15RPC column and eluted with a fragmented gradient A (0.1% TFA) and B (0.085% TFA in 60% acetonitrile) using a LKB Purifier (Amersham Pharmacia Biotech, Piscataway, N.J). The active fractions were pooled and dried in a lyophilizer. The pellet was redissolved in 0.25% TFA and subjected to a second round purification using a fragmented gradient of buffer A (0.1% TFA) and B (0.085% TFA in 80% methanol). The single active peak fraction was collected, dried in a lyophilizer, and used for sequence analysis and electrospray ionization mass spectrometry (EIMS).

Chemical Modification of Mutacin I

Fifty micrograms of purified mutacin I were dried under vacuum and resuspended in 90 μl of a derivatization mixture consisting of 280 μl ethanol, 200 μl water, 65 μl 5M sodium hydroxide, and 60 μl ethanethiol as described). Meyer et al. (1994) *Anal Biochem.* 223:185–190. The reaction proceeded at 50° C. for one hour under nitrogen, then stopped by the addition of 2 μl acetic acid. The reaction mixture was dried under vacuum and washed three times with 50% ethanol. The pellet was resuspended in 10 μl of 50% acetonitrile with 1% formic acid for EIMS analysis and peptide sequencing by Edman degradation.

Nucleic Acid Accession Numbers

The sequence for the mutacin I operon has been submitted to Genbank with the accession #AF207710 (AF267498), also designated SEQ ID No: 3.

RESULTS

Cloning and Sequencing of the Mutacin I Biosynthetic Genes

As described previously (Qi et al. (1999) *Appl. Environ. Microbiol.* 65:652–658), while isolating mutacin III biosynthesis genes by PCR amplification using a pair of primers designed based on the conserved sequences among LanA and LanB proteins, the mutacin I biosynthesis genes were isolated using the same primers. Sequencing of the isolated PCR fragment demonstrated a striking similarity between the mutacin I and mutacin III genes. By chromosomal walking, the major part of the mutacin I biosynthesis operon was cloned and sequenced as shown in FIG. 1A. It consists of eight genes in the order of mutR, -A, -A', -B, -C, -D, -P, and -T, which is possibly followed by the immunity gene mutF (SEQ ID No: 12). As in the mutacin III operon, MutR (SEQ ID No: 4) was the positive regulator for the expression of the mutacin I operon (Qi et al. (1999) *Appl. Environ. Microbiol.* 65:652–658. MutA (SEQ ID No: 5) and MutA' (SEQ ID No: 6) showed strong similarity to each other as shown in FIG. 1B. Insertional inactivation of mutA and mutA' demonstrated that mutA was required for mutacin I production, while mutA' was not as shown in FIG. 1C. This result suggested that, like mutA in the mutacin III operon, the mutA in the mutacin I operon was likely the structural gene encoding prepromutacin I. MutB (SEQ ID No: 7), -C (SEQ ID No: 8) and -D (SEQ ID No: 10) possibly constituted the modification apparatus for prepromutacin I, and MutT (SEQ ID No: 11) and -P (SEQ ID No: 10) are the ABC transporter and protease for transportation and processing of premutacin I, respectively. Other gene encoded mutacin I peptides include MutF (SEQ ID No: 12), MutE (SEQ ID No: 13), MutG (SEQ ID No: 14), OrfX (SEQ ID No: 15), OrfY (SEQ ID No: 16), and OrfZ (SEQ ID No: 17).

Similarity Between Mutacin I and Mutacin III Biosynthesis Genes

The overall similarity between mutacin I and mutacin III biosynthesis genes was ~94% at the nucleotide level over the 10 kb operon. However, the differences between the two operons were not distributed evenly among the different genes. For example, from mutR to the region immediately upstream of mutA, the similarity was 99%, while in the mutA and mutA' coding regions, the similarity was only 89% and 91%, respectively. At the amino acid level, the two MutAs shared 84% identical residues as shown in FIG. 2, and the two MutA's shared 93% identical residues. For MutB and MutC the similarity was 93% and 95%, respectively. An even higher similarity (99%) existed in MutP and -T between the two strains.

Purification of Mutacin I

To biochemically characterize mutacin I, sufficient amount of starting material is required. Applicants' first attempt to isolate mutacin I from liquid culture failed because no mutacin I was produced in any of the liquid cultures that were tested. A stab culture on TH/agarose plate as described for mutacin III was then tried. Qi et al. (1999) *Appl. Environ. Microbiol.* 65:652–658. Mutacin I was produced on such a plate, however the production level was still too low for satisfactory isolation. Based on the observation that mutacin I could be produced on all solid media plates regardless of the media composition, it was reasoned that the production of mutacin I may be regulated by a cell-density mediated control mechanism similar to quorum sensing. (Kleerebezem et al. (1997) *Mol. Microbiol.* 24:895–904; Surette et al. (1999) *Proc. Nati. Acad. Sci. USA* 96:1639–1644). Based on this rationale, a membrane transfer technique as described in Materials and Methods was employed, which resulted in a high level of mutacin I production.

Figure 3A:
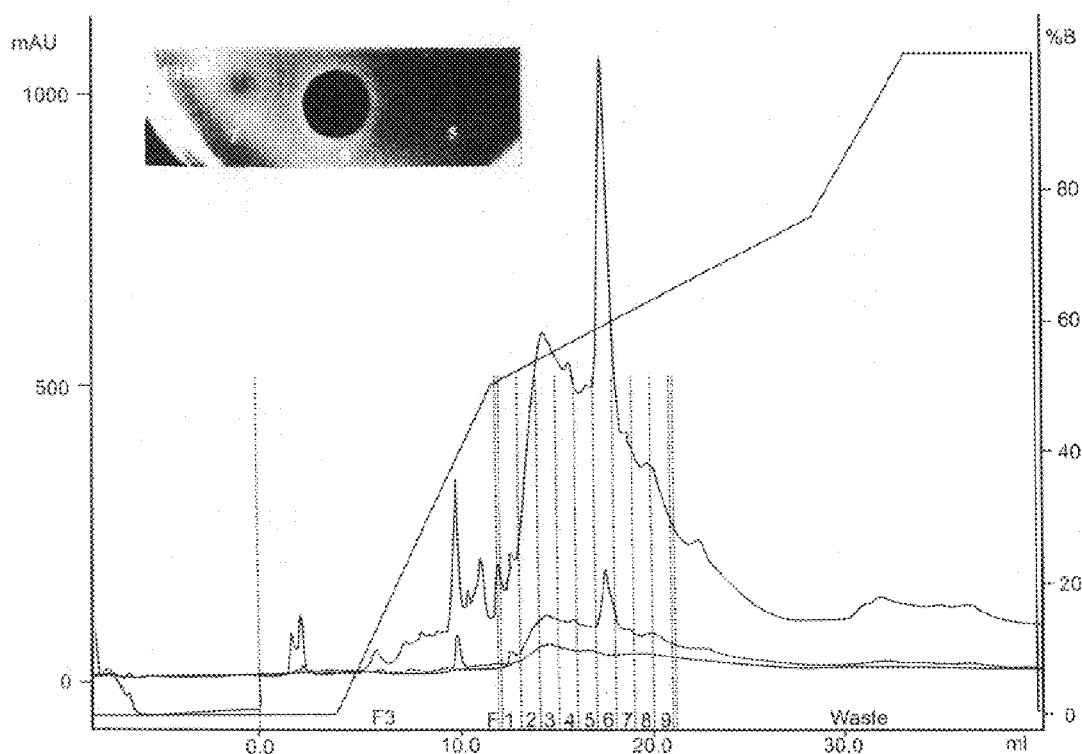
FIGS. 3A–3C. Purification and EIMS analysis of mutacin I. (A) Elution profile of the first round purification of crude extract of mutacin I by reverse phase HPLC. One-ml fractions were collected along the course of elution and tested for antimicrobial activity (insert). (B) Elution profile of the second round purification using pooled fraction 6 from the first pass as starting material. Fractions 6 and 7 were active. (C) Electrospray ionization mass spectrometry (EIMS) of the purified mutacin I. The mass to charge ratio (m/z) for the doubly-charged molecule (1183) and the triply-charged molecule (788) are labeled. The estimated molecular weight was 2364 Da.
Figure 3B:
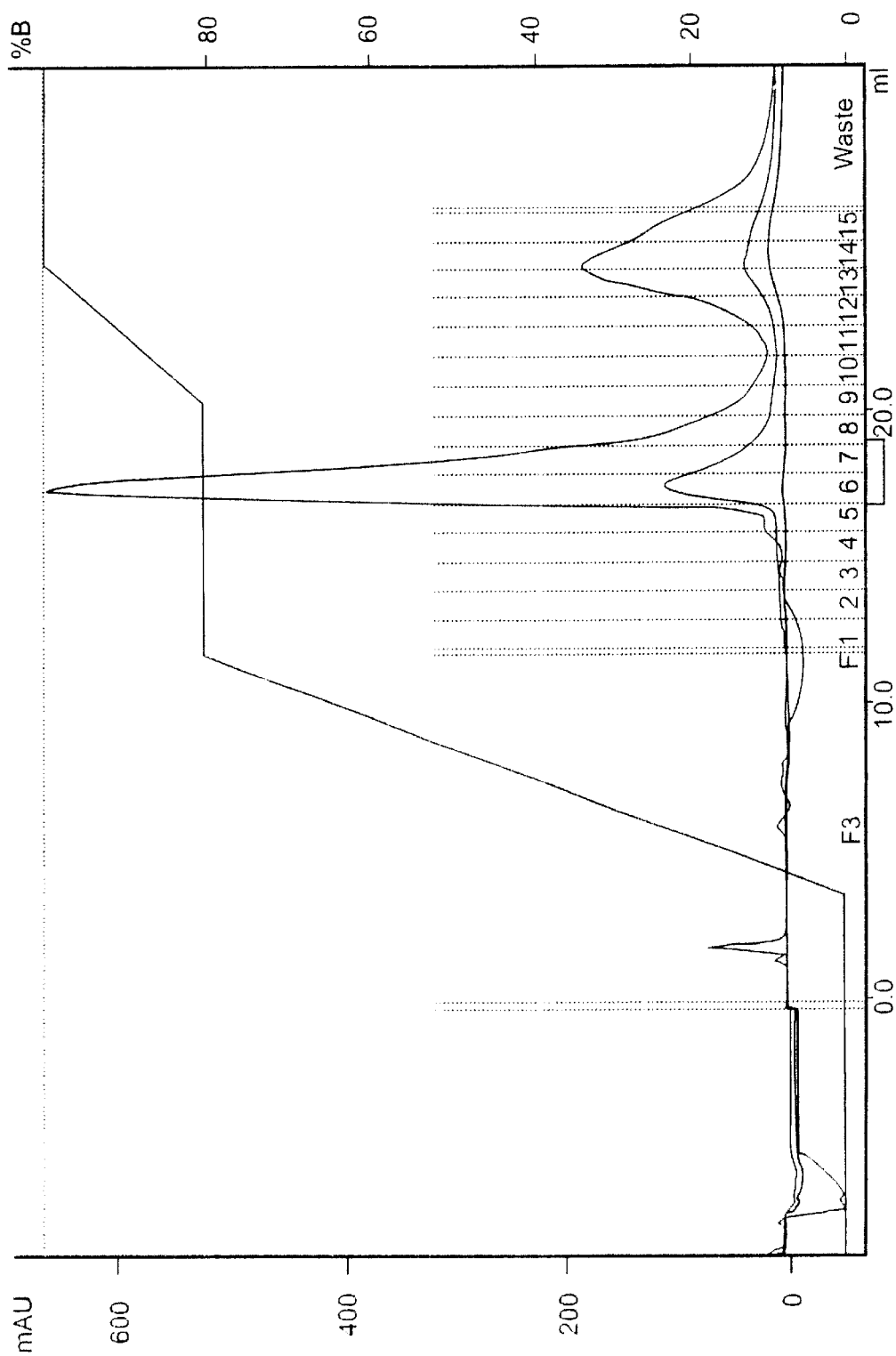
Figure 3C:
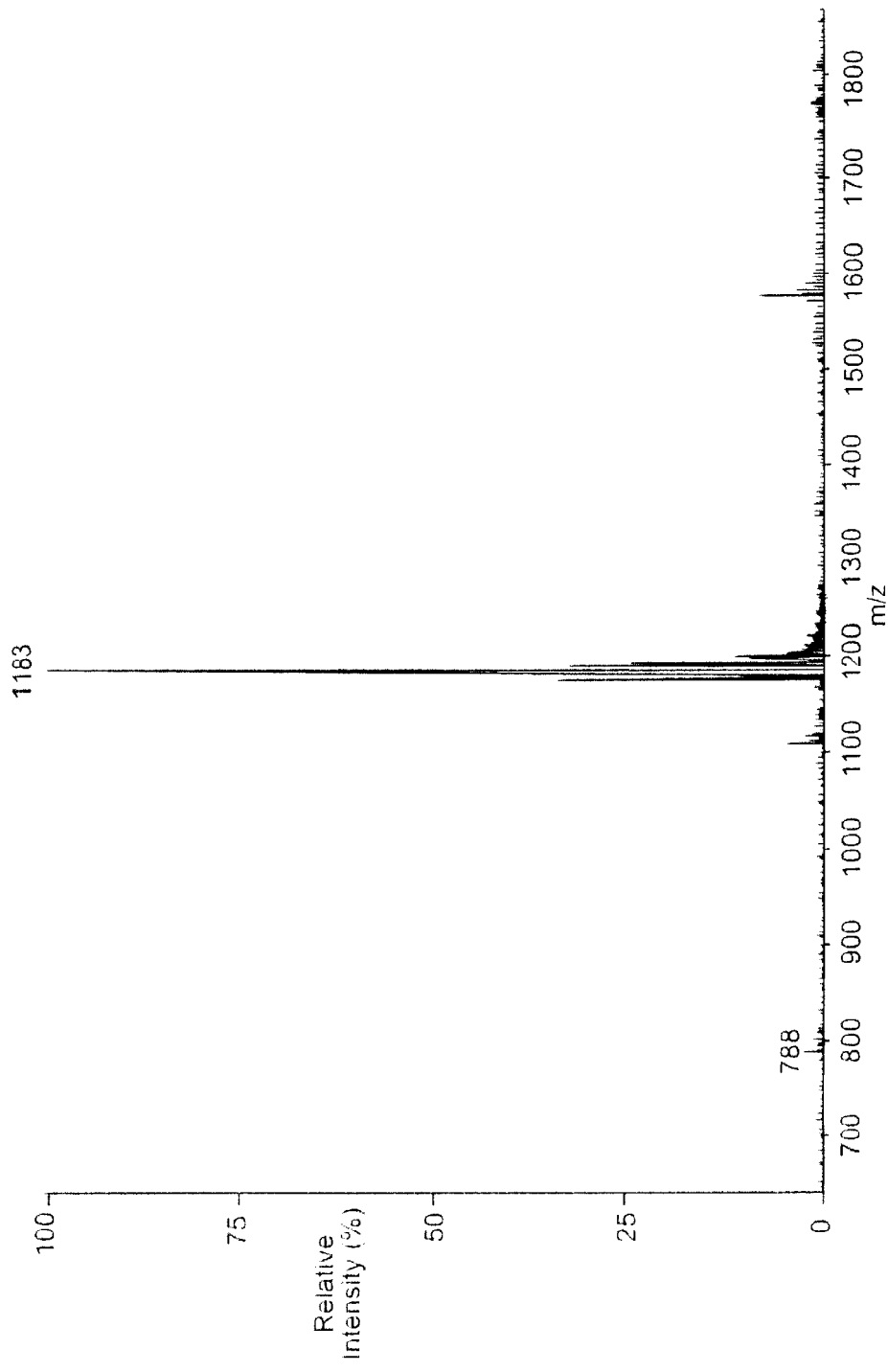

Mutacin I was purified by reverse-phase HPLC as shown in FIG. 3. The active fraction (fraction 6) from the first pass (see FIG. 3A) was collected and subjected to a second round purification using a different buffer B and a different gradient (see FIG. 3B). The active fractions (fractions 6 and 7) from the second pass were dried under vacuum and tested for purity by EIMS analysis. As shown in FIG. 3C, mutacin I was purified to near homogeneity as judged by the lack of significant background peaks in the MS chromatogram.

Characterization of Mutacin I by Ethanethiol Derivatization and MS Analyses

The molecular weight of mutacin I was measured by electrospray ionization mass spectrometry. The mass-to-charge ratio for the doubly-charged molecule was 1183, and that for the triply-charged molecule was 788 as shown in FIG. 3C. Thus the measured molecule mass was 2364 Da. This value was in a good agreement with the calculated value of 2516 Da for the unmodified mutacin I minus six molecules of water (108 Da) and one molecule of carboxy residue (45 Da from decarboxylation at the C-terminal cycteine residue).

The primary sequence of mutacin I contained six serine residues and one threonine residue, all of which were potential sites for post-translational dehydration. To confirm that there were indeed six dehydrated residues in the mature mutacin I, an ethanethiol modification of mutacin I under alkaline conditions was performed. In this reaction, one molecule of ethanethiol could insert into the thioether bridge, resulting in a S-ethylcystein and a cystein, or it could insert into the double bound of a dehydrated serine or threonine to form a S-ethylcystein or a P-methyl-S-ethylcycteine. Meyer et al. (1994) *Anal. Biochem.* 223:185–190; Novak et al. (1996) *Anal Biochem.* 236:358–360. Ethanethiol derivatization of lantibiotics has been used prior to sequencing of the other lantibiotic gallidermin and pep5 (Meyer et al. (1994) *Anal. Biochem.* 223:185–190), and for determination of the number of dehydrated amino acid residues in mutacin II (Novak et al. (1996) *Anal. Biochem.* 236:358–360). The expected molecular mass of mutacin I after each addition of an ethanethiol molecule is listed in Table 1.

TABLE 1

Expected molecular masses of ethanethiol derivatives of mutacins I and III

| Mutacin | Expected mass (Da) | | | | | | |
|---|---|---|---|---|---|---|---|
| | 0* | 1 | 2 | 3 | 4 | 5 | 6 |
| I | 2,364 | 2,426 | 2,487 | 2,549 | 2,611 | 2,673 | 2,738 |
| III | 2,264 | 2,318 | 2,390 | 2,452 | 2,514 | 2,576 | 2,638 |

*Number of ethanethiol molecules added.

Figure 4A:
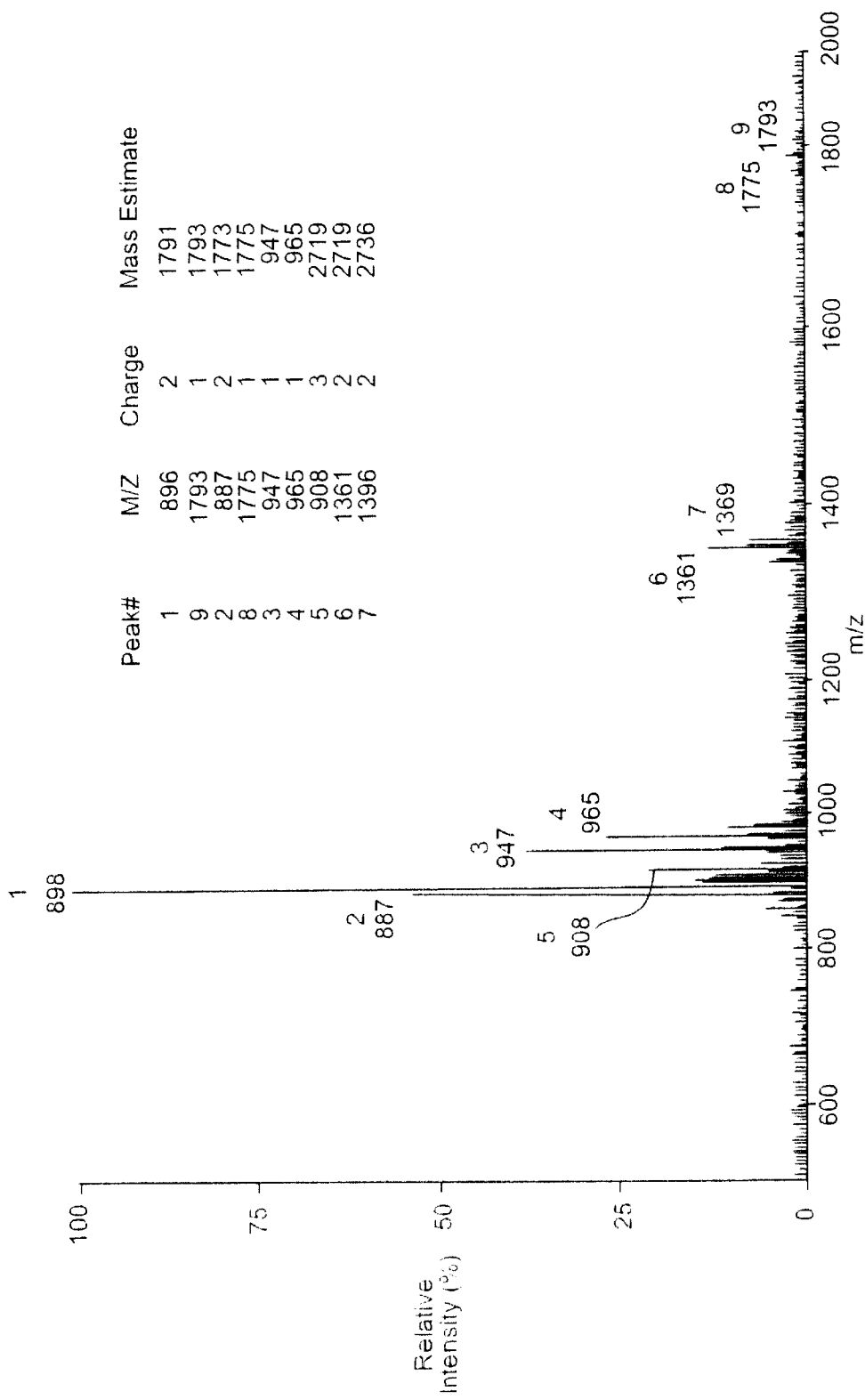
Figure 4C:
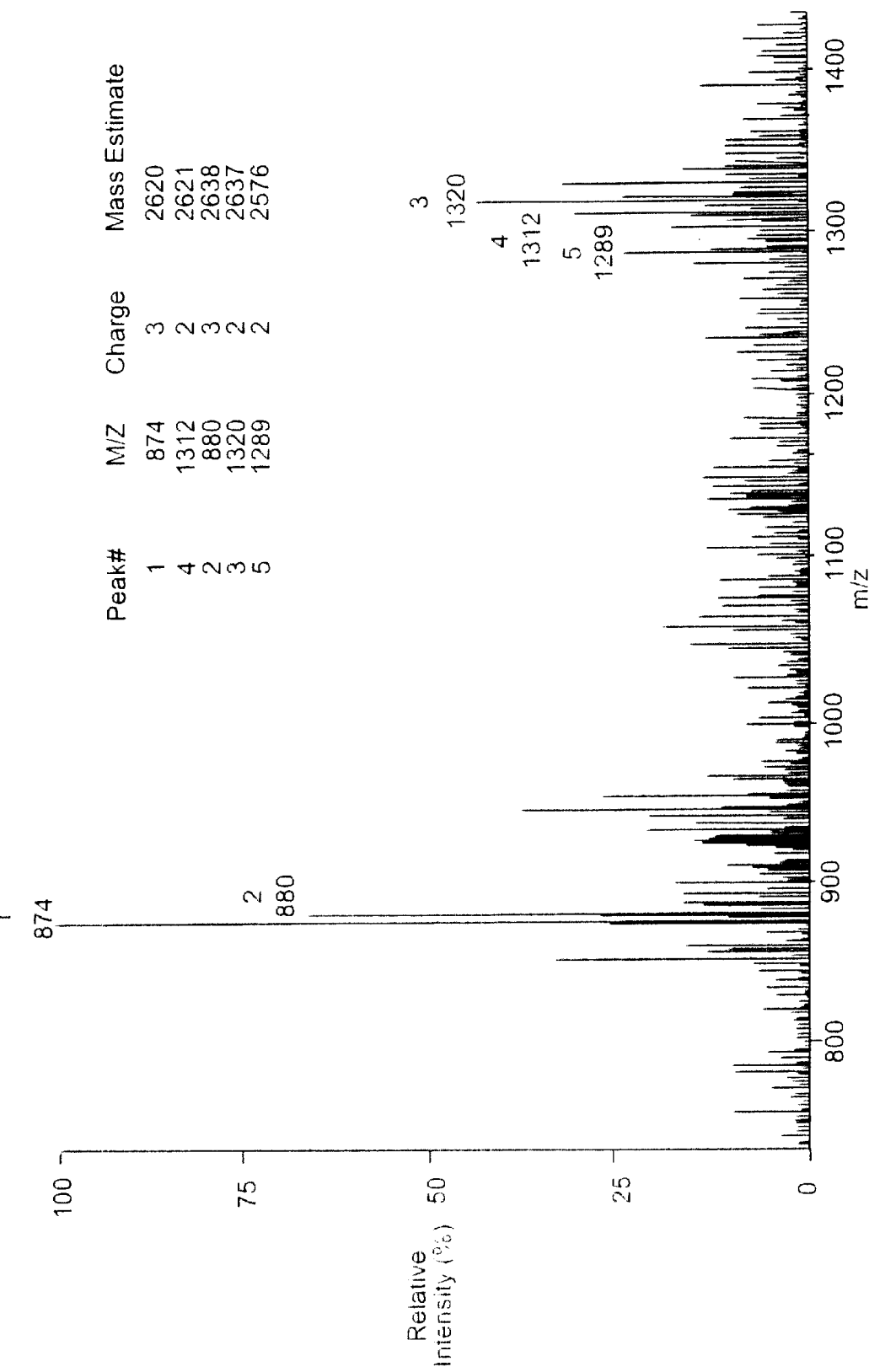

Quite surprisingly, none of the major peaks generated after ethanethiol modification of mutacin I had the expected molecular mass as shown in FIG. 4A. A very small portion of the molecules showed a pass of 2736 Da (Peak 7), which could account for mutacin I plus six molecules of ethanethiol (2364+62×6); the result of the molecules were all much smaller than expected. With close inspection and calculations, the identity of the small molecules was determined. As shown in FIG. 4B, it appeared that the majority of mutacin I molecules broke into two fragments after the addition of six molecules of ethanethiol. The larger fragment with a mass of 1791 Da was the N-terminal part from F-1 to N-16, and the smaller fragment (965 Da) was the C-terminal part from P-17 to C-24. This finding was of interest because the closely related mutacin III molecule remained intact after the same modification reaction under the same conditions as shown in FIG. 4C.

Peptide Sequencing of Unmodified and Ethanethiol Modified Mutacin I

Comparison of mutacin I and mutacin III revealed that mutacin I had seven potential dehydration sites (six serines and one threonine), while mutacin III had six (four serines and two threonines). Interestingly, both mutacins had six ethanethiol additions after ethanethiol modification (see FIGS. 4A and 4C), suggesting that all serine or threonine residues in mutacin III were dehydrated. To determine which serine or threonine residue was not dehydrated in mutacin I, the purified mutacin I was subjected to peptide sequencing by Edman degradation. With native mutacin I, Edman degradation was blocked after the first F residue, suggesting that the second serine residue is dehydrated. Dehydrated amino acids were shown to block Edman degradation in other lantibiotics. Gross et al. (1971) *J. Am. Chem. Soc.* 93:4634–4635; Mota-Meira et al. (1997) *FEBS Lett.* 410:275–279; Novak et al. (1994) *J. Bacteriol.* 176:4316–4320.

To get a complete sequence of mutacin I, the ethanethiol-derivatized mutacin I had to be used. Ethanethiol-derivatization of lantibiotics was shown to allow Edman degradation to proceed through the dehydrated serine and threonine residues and thioether bridges in other lantibiotics. Meyer et al. (1994) *Anal. Biochem.* 223:185–190; Mota-Meira et al. (1997) *FEBS Lett.* 410:275–279. Since the majority of mutacin I molecules was broken into two fragments (see FIG. 4) during ethanethiol modification, the C-terminal fragment had to be eliminated to solve the problem of having two N-termini in the reaction mixture. After several trials, the C-terminal fragment was eliminated by washing the reaction mixture with 30% acetonitrile. The pellet fraction after 30% acetonitrile wash contained mostly the full-length modified mutacin I and the N-terminal fragment Sequencing of the pellet fraction revealed the following sequence: $F_1$-$SEC_2$-$SEC_3$-$L_4$$SEC_5$-$L_6$-$SEC_7$-$SEC_8$-$L_9$-$G_{10}$-$SEC_{11}$-$T_{12}$-$G_{13}$-$V_{14}$-$K_{15}$-$N_{16}$-$P_{17}$-$SEC_{18}$-$F_{19}$-$N_{20}$-$SEC_{21}$-$Y_{22}$-$SEC_{23}$. S-ethylcysteine (SEC) was the product of ethanethiol insertion into the double bond of dehydrated serine, or the thioether bridge in lanthionine. The results revealed that all six serine residues in the mutacin I molecule were dehydrated, and that T-12 remained as a nondehydrated residue. In addition, a closer look at the HPLC chromatogram of the sequencing reaction of mutacin I revealed minor peaks in the sequence of P-x-F-N-x-Y. This sequence correlated with the C-terminal fragment of mutacin I: $P_{17}$-$S_{18}$-$F_{19}$-$N_{20}$-$S_{21}$-$Y_{22}$-$C_{23}$-$C_{24}$. This result corroborated the previous assignment for the two peptide fragments generated during ethanethiol modification as shown in FIG. 4B.

The mutacin I biosynthesis genes from the group I strain of *S. mutans* CH43 were cloned and sequenced. DNA and protein sequence analysis revealed that mutacin I and mutacin III are highly homologous to each other, likely arising from a common gene ancestor. Mutacin I was produced by a membrane transfer technique and purified to homogeneity by reverse phase HPLC. The mature mutacin I is twenty-four amino acids in size with a molecular weight of 2364 Da. Ethanethiol modification of mutacin I revealed that it contains six dehydrated amino acids. Sequencing of the native and ethanethiol-derivatized mutacin I by Edman degradation demonstrated that mutacin I is encoded by mutA, and that the six serine residues in the primary sequence of mutacin I are dehydrated, four of which are possibly involved with thioether bridge formation. Comparison of the primary sequence of mutacin I with that of mutacin III and epidermin suggests that mutacin I likely possesses the same bridging pattern as epidenmin.

A closer inspection of the differences between the homologous genes of mutacin I and mutacin III revealed that they are not all distributed evenly. For MutR, -D, -P, and -T, the homology is over 99% between the two mutacins, while for MutA, -A', -B, and -C, the similarity varies from 87 to 95%. The distribution of the variations within a protein is not even either. For example, in MutA, the leader peptide region was identical between the two mutacins. However, the mature peptide region differed by 37.5% (FIG. 2). More interestingly, the sequence of the mature mutacin III is closer to that of epidermin (77% similarity) than to mutacin I (62.5% similarity), while the sequence of the leader peptide of mutacin III and epidennin are dramatically different as seen in FIG. 2. For MutB, -C, -D, -P, and -T proteins, mutacin I and mutacin III are closer to each other than to epidermin.

The biosynthesis of lantibiotics involves several post-translational modification steps. Chakicherla et al. (1995) *J. Biol. Chem.* 270:23533–23539; de Vos et al. (1995) *Molecular Microbiol.* 17:427–437; Sahl et al. (1998) *Annu. Rev. Microbiol.* 52:41–79. The first step is the translation of the structural gene message into a prepropeptide. The prepropeptide is then modified by dehydration of serine and threonine residues, and formation of thioether bridges between cysteine and the dehydrated amino acid residues. The prepeptide is then translocated across the cell membrane, where the leader peptide is cleaved off and the mature peptide released to the outside medium.

One advantage of lantibiotics over classical antibiotics is its gene-encoded nature, which means that lantibiotics can be altered with ease by manipulating the structural genes through mutagenesis. In reality, however, the number of mutations that can be made is limited because the production of active lantibiotics depends on correct post-translational modification and processing.

Mutacin I and mutacin III are closely related to each other at both the nucleotide and amino acid levels. Comparison of the mature peptide sequence of mutacin I and mutacin III suggests that they may also have the same pattern of thioether bridge formation. Despite all the similarities, some important differences exist between the two mutacins. For example, ethanethiol modification of mutacin I broke the molecule into two fragments between N-16 and P-17 as shown in FIG. 4B, while the same reaction did not affect the integrity of mutacin III as shown in FIG. 4C. Comparison of the two mutacins revealed that the major difference is at the linker region (T-12 to P-17), where mutacin I has the sequence T-G-V-K-N-P, and mutacin III has the sequence A-R-T-G as shown in FIG. 2A. These different amino acid residues, according to the statistical figures of Creighton (Creighton, p. 235, in (ed.) Proteins: Structures and molecular principles, W. H. Freeman and Company, New York), have different tendencies in forming different secondary structures in proteins. For example, N-16 and P-17 in mutacin I are more likely to be involved in forming β-turns, while A-12 in mutacin III is more likely to participate in α-helix formation (Stryer, p. 37, in (ed.) Biochemistry, W. H. Freeman and Company, Biochemistry, New York). More importantly, N-16 and P-17 are absent in mutacin III.

In accordance with the possible difference in secondary and tertiary structures, mutacin I and mutacin III have different hydrophobicity and antimicrobial activity. In reverse-phase HPLC analysis, mutacin I is eluted at a higher acetonitrile concentration than mutacin III, suggesting that it is more hydrophobic than mutacin III. In antimicrobial spectrum assays with a limited set of pathogens, mutacin III is more potent than mutacin I against *Staphylococcus aureus* and *Staphylococcus epidermidis*, while both mutacins have equal activities against other pathogens such as enterococci, pneumococci, and Group A streptococci.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A purified and isolated nucleic acid fragment coding for a lantibiotic as set forth in SEQ ID No: 1.

2. A vector which comprises the nucleic acid of claim 1.

3. A prokaryotic or eukaryotic host cell transformed or transfected with the vector of claim 2.

4. An isolated and purified DNA fragment comprising a protein coding sequence encoding the expression of the protein of SEQ ID No: 2.

* * * * *

UNITED STATES PATENT AND TRADEMARK OFFICE
CERTIFICATE OF CORRECTION

PATENT NO.     : 6,342,385 B1
DATED          : January 29, 2002
INVENTOR(S)    : Fengxia Qi et al.

It is certified that error appears in the above-identified patent and that said Letters Patent is hereby corrected as shown below:

Title page,
Item [56], FOREIGN PATENT DOCUMENTS, replace "GB" with -- WO --.

Column 2,
Line 14, replace "gallidennin" with -- gallidermin --.
Line 18, replace "Biol" with -- Biol. --.
Line 22, replace "Appl" with -- Appl. --.
Line 22, replace "Microbiol" with -- Microbiol. --.
Line 38, replace "Appl" with -- Appl. --.
Line 50, replace "-A';" with -- -A; --.
Line 53, replace "galliderniin" with -- gallidermin --.

Column 4,
Line 21, replace "mutacin II" with -- mutacin III --.

Column 5,
Line 17, replace "cloning." with -- cloning: --.

Column 7,
Line 16, after "microorganisms" start new paragraph.

Column 8,
Line 53, before "in combination" insert -- or --.

Column 10,
Line 33, replace "Appl" with -- Appl. --.

Column 12,
Line 20, replace "Nati" with -- Natl --.
Line 57, replace "P-methyl-S-ethylcycteine" with -- B-methyl-S-ethylcycteine --.
Line 59, replace "Anal" with -- Anal. --

UNITED STATES PATENT AND TRADEMARK OFFICE
CERTIFICATE OF CORRECTION

PATENT NO. : 6,342,385 B1
DATED : January 29, 2002
INVENTOR(S) : Fengxia Qi et al.

It is certified that error appears in the above-identified patent and that said Letters Patent is hereby corrected as shown below:

Column 13,
Line 64, replace "$L_4SEC_5$" with -- $L_4\text{-}SEC_5$ --.

Column 14,
Line 41, replace "epidennin" with -- epidermin --.

Column 15,
Line 12, replace "molecular principles" with -- Molecular Principles --.

Signed and Sealed this

Twenty-ninth Day of April, 2003

JAMES E. ROGAN
*Director of the United States Patent and Trademark Office*